United States Patent
Arnold et al.

(10) Patent No.: US 10,717,960 B2
(45) Date of Patent: Jul. 21, 2020

(54) BIOTECHNOLOGICAL APPARATUS COMPRISING A BIOREACTOR, EXHAUST GAS TEMPERATURE CONTROL DEVICE FOR A BIOREACTOR AND A METHOD FOR TREATING AN EXHAUST GAS STREAM IN A BIOTECHNOLOGICAL APPARATUS

(71) Applicant: DASGIP INFORMATION AND PROCESS TECHNOLOGY GMBH, Jülich (DE)

(72) Inventors: Matthias Arnold, Aachen (DE); Heinz Gerhard Köhn, Hamburg (DE); Nico Gülzow, Hamburg (DE); Sven Eikelmann, Petershagen (DE); Guido Ertel, Dormagen (DE); Sebastian Selzer, Aachen (DE)

(73) Assignee: DASGIP INFORMATION AND TECHNOLOGY GMBH, Julich (DE)

( * ) Notice: Subject to any disclaimer, the term of this patent is extended or adjusted under 35 U.S.C. 154(b) by 44 days.

(21) Appl. No.: 14/351,086

(22) PCT Filed: Oct. 10, 2012

(86) PCT No.: PCT/EP2012/070095
§ 371 (c)(1),
(2) Date: Apr. 10, 2014

(87) PCT Pub. No.: WO2013/053779
PCT Pub. Date: Apr. 18, 2013

(65) Prior Publication Data
US 2014/0329224 A1    Nov. 6, 2014

Related U.S. Application Data

(60) Provisional application No. 61/660,522, filed on Jun. 15, 2012.

(30) Foreign Application Priority Data

Oct. 10, 2011  (DE) .................... 10 2011 054 364
Jun. 15, 2012  (EP) .................... 12172291

(51) Int. Cl.
C12M 1/02       (2006.01)
C12M 3/00       (2006.01)
(Continued)

(52) U.S. Cl.
CPC ............ *C12M 41/18* (2013.01); *C12M 23/28* (2013.01); *C12M 23/46* (2013.01); *C12M 41/00* (2013.01); *C12M 47/20* (2013.01)

(58) Field of Classification Search
CPC ...... C12M 23/28; C12M 23/46; C12M 41/18; C12M 47/20
(Continued)

(56) References Cited

U.S. PATENT DOCUMENTS 5,342,781 A * 8/1994 Su .................... C12M 27/20
                                                        210/194
5,443,985 A    8/1995 Lu et al.
(Continued)

FOREIGN PATENT DOCUMENTS

DE           2350264 A1      4/1974
DE     10 2004 047 560       2/2006
(Continued)

OTHER PUBLICATIONS

Miyajima Kazuhisa, English language translation of JP 2003-032865A, translated on Dec. 31, 2015.*
(Continued)

*Primary Examiner* — Liban M Hassan
(74) *Attorney, Agent, or Firm* — Merchant & Gould P.C.

(57) ABSTRACT

This patent document relates to the field of biotechnological apparatuses. It relates particularly to a biotechnological
(Continued)

Figure 1:
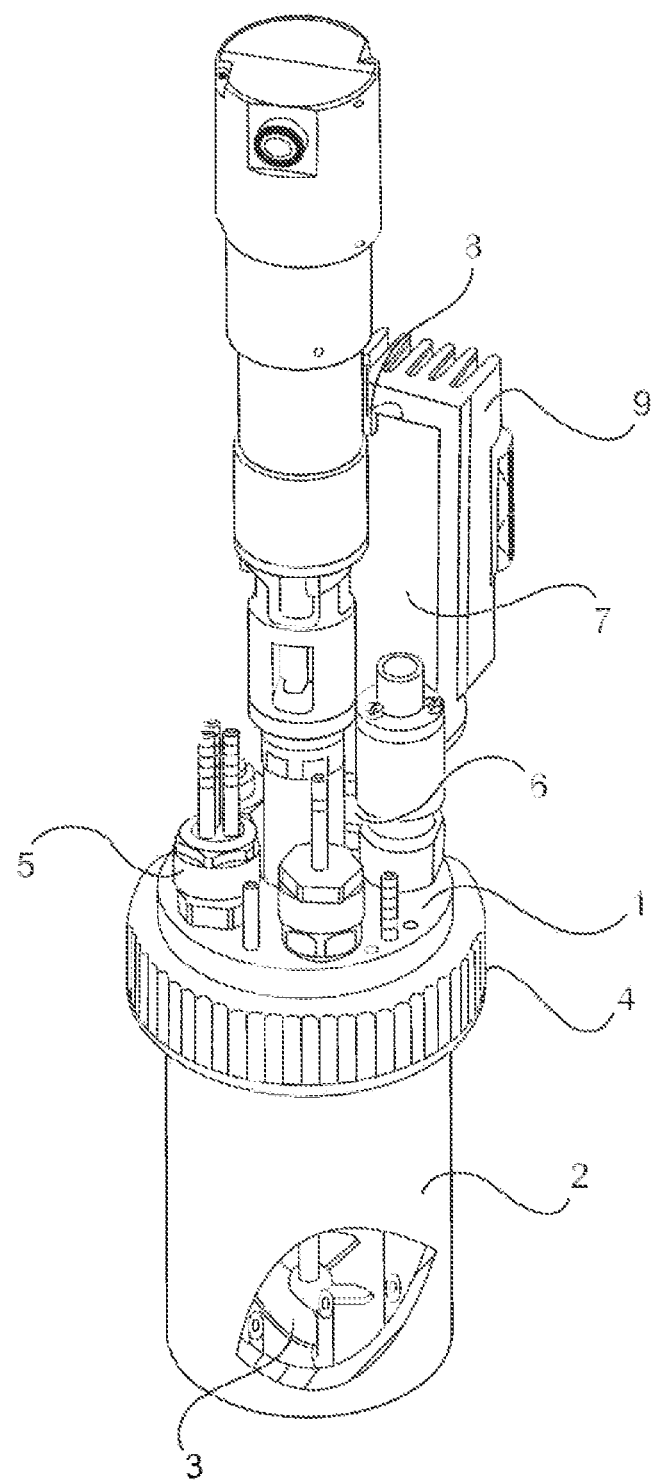

apparatus comprising a bioreactor, an exhaust gas temperature control device and a method for treating an exhaust gas stream. This patent document further relates to a connection device for a sterile single-use fluid conduit of a single-use bioreactor and to a method for treating a fluid stream. The reusable connection device comprises a receptacle in which a portion of the fluid conduit can be detachably arranged, and a coupling member connecting the connection device to a temperature control device, the receptacle having a contact surface which is arranged such that the contact surface abuts a fluid conduit arranged in the receptacle, and wherein a portion of a fluid conduit can be introduced into the receptacle in a direction running substantially orthogonally to a longitudinal axis of the connection device.

12 Claims, 17 Drawing Sheets

(51) Int. Cl.
*C12M 1/00* (2006.01)
*C12M 1/34* (2006.01)

(58) Field of Classification Search
USPC .......................................... 435/286.1, 289.1
See application file for complete search history.

(56) References Cited

U.S. PATENT DOCUMENTS

| | | | |
|---|---|---|---|
| 5,949,958 A * | 9/1999 | Naperkowski | A61L 2/07 392/399 |
| 6,133,021 A * | 10/2000 | Gu | G01N 33/1866 435/288.7 |
| 6,202,713 B1 | 3/2001 | Drescher et al. | |
| 6,432,698 B1 * | 8/2002 | Gaugler | C12M 23/14 435/296.1 |
| 7,007,352 B1 | 3/2006 | Hill | |
| 7,591,953 B2 * | 9/2009 | Pellikka | C07K 1/13 210/650 |
| 8,012,741 B2 | 9/2011 | Schlafer | |
| 8,522,996 B2 | 9/2013 | Beese et al. | |
| 2001/0004879 A1 | 6/2001 | Umotoy et al. | |
| 2003/0079787 A1 | 5/2003 | Heise | |
| 2003/0119201 A1 | 6/2003 | Wolfram et al. | |
| 2004/0029170 A1 | 2/2004 | Wolfram et al. | |
| 2004/0253716 A1 | 12/2004 | Jaeger et al. | |
| 2005/0032211 A1 | 2/2005 | Shaaltiel | |
| 2006/0042571 A1 | 3/2006 | Panasik et al. | |
| 2007/0251714 A1 | 11/2007 | Winkelbach et al. | |
| 2007/0253288 A1 | 11/2007 | Mennenga et al. | |
| 2008/0139865 A1 | 6/2008 | Galliher et al. | |
| 2008/0265561 A1 | 10/2008 | Buchanan et al. | |
| 2009/0075362 A1 | 3/2009 | Baumfalk et al. | |
| 2009/0275121 A1 | 11/2009 | Greller et al. | |
| 2009/0311776 A1 | 12/2009 | Kelly, Jr. et al. | |
| 2010/0028990 A1 | 2/2010 | Broadley et al. | |
| 2010/0170400 A1 | 7/2010 | Van Den Boogard et al. | |
| 2010/0290184 A1 | 11/2010 | Tani | |
| 2011/0003374 A1 | 1/2011 | Van Den Boogard et al. | |
| 2011/0058447 A1 | 3/2011 | Reif et al. | |
| 2011/0058448 A1 | 3/2011 | Reif et al. | |
| 2011/0076759 A1 * | 3/2011 | Reif | C12M 21/04 435/297.1 |
| 2011/0207218 A1 | 8/2011 | Staheli et al. | |
| 2012/0003733 A1 | 1/2012 | Gueneron | |
| 2012/0103579 A1 | 5/2012 | Reif et al. | |

FOREIGN PATENT DOCUMENTS

| | | |
|---|---|---|
| DE | 20 2007 005 399 | 8/2007 |
| DE | 20 2007 005 868 | 8/2007 |
| DE | 10 2006 021 984 | 11/2007 |
| DE | 20 2009 006 839 | 8/2009 |
| DE | 10 2008 027 638 | 12/2009 |
| DE | 10 2010 001 779 | 8/2011 |
| DE | 10 2011 054 363 | 4/2013 |
| DE | 10 2011 054 364 | 4/2013 |
| DE | 10 2011 054 365 | 4/2013 |
| EP | 2 141 224 | 1/2010 |
| EP | 2 251 407 | 11/2010 |
| EP | 2586857 A1 | 5/2013 |
| EP | 2 674 479 | 12/2013 |
| GB | 1446412 A | 8/1976 |
| GB | 1578015 | 10/1980 |
| GB | 2464303 | 4/2010 |
| GB | 2465282 | 5/2010 |
| JP | 61-008000 U1 | 1/1986 |
| JP | 63-032476 A | 2/1988 |
| JP | 2001-330356 A | 11/2001 |
| JP | 2003-032865 A | 1/2003 |
| JP | 2003-500206 A | 1/2003 |
| JP | 2003032865 A * | 1/2003 |
| JP | 2003-110155 A | 4/2003 |
| JP | 2004-160434 A | 6/2004 |
| JP | 2005-216729 A | 8/2005 |
| JP | 2008-501347 A | 1/2008 |
| JP | 2008-511457 A | 4/2008 |
| JP | 2008-514171 A | 5/2008 |
| JP | 2009-539408 A | 11/2009 |
| JP | 2009-543553 A | 12/2009 |
| JP | 2010-267173 A | 11/2010 |
| JP | 2012-170364 A | 9/2012 |
| KR | 10-2004-0048734 | 6/2004 |
| WO | WO 99/02961 | 1/1999 |
| WO | 00/72973 A1 | 12/2000 |
| WO | WO 00/72973 A1 | 12/2000 |
| WO | 2005/118771 A2 | 12/2005 |
| WO | WO 2005/118771 A2 | 12/2005 |
| WO | WO 2005/123258 | 12/2005 |
| WO | WO 2008/088371 A2 | 7/2008 |
| WO | WO 2008/088379 | 7/2008 |
| WO | WO 2008/088379 A2 | 7/2008 |
| WO | WO 2009146769 A2 * | 12/2009 ............ C12M 21/04 |
| WO | WO 2011/036276 | 3/2011 |
| WO | WO 2011/041508 | 4/2011 |
| WO | WO 2011/079180 | 6/2011 |
| WO | WO 2013/053778 | 4/2013 |
| WO | WO 2013/053779 | 4/2013 |
| WO | WO 2013/150064 | 10/2013 |
| WO | WO 2013/186294 | 12/2013 |

OTHER PUBLICATIONS

Japanese Examination Report for Japanese Application No. 2014-535057, dated Aug. 27, 2015.
Chinese Search Report dated Jan. 8, 2015 for corresponding Chinese Patent Application No. 201280060936.2, filed Oct. 10, 2012, 2 pages.
Chinese Examination Report dated Jan. 16, 2015 for corresponding Chinese Patent Application No. 201280060936.2, filed Oct. 10, 2012, 12 pages.
International Search Report and Written Opinion from International Application No. PCT/EP2012/070095 dated Feb. 25, 2013. 23552 Patent Trademark Office.
Decision of Refusal from related Japanese Patent Application No. 2014-535057, dated Jun. 2016.
International Preliminary Report on Patentability from International Application No. PCT/EP2012/070095 dated Apr. 24, 2014.
Office Action from corresponding Japanese Patent Application No. 2016-198828, dated Sep. 19, 2017.

* cited by examiner

BIOTECHNOLOGICAL APPARATUS COMPRISING A BIOREACTOR, EXHAUST GAS TEMPERATURE CONTROL DEVICE FOR A BIOREACTOR AND A METHOD FOR TREATING AN EXHAUST GAS STREAM IN A BIOTECHNOLOGICAL APPARATUS

This application is a National Stage Application of PCT/EP2012/070095, filed 10 Oct. 2012, which claims benefit of U.S. Provisional Ser. No. 61/660,522, filed 15 Jun. 2012, and which claims benefit of Ser. No. 12/172,291.2, filed 15 Jun. 2012 in Europe, and which claims benefit of Ser. No. 10 2011 054 364.3, filed 10 Oct. 2011 in Germany, and the entire disclosures of these applications are incorporated herein by reference. To the extent appropriate, a claim of priority is made to each of the above disclosed applications.

The invention relates to the field of biotechnological apparatuses. It relates in particular to a biotechnological apparatus comprising a bioreactor, an exhaust gas temperature control device for a bioreactor and a method for treating an exhaust gas stream in a biotechnological apparatus comprising a bioreactor.

The invention further relates to a reusable connection device for a sterile single-use fluid conduit, in particular for a sterile single-use exhaust gas tube, of a single-use bioreactor and to a reusable temperature control device for controlling the temperature of a sterile single-use fluid conduit of a single-use bioreactor, a biotechnological device comprising a single-use bioreactor with a sterile single use fluid conduit and a method for treating a fluid stream in a biotechnological device.

BACKGROUND OF THE INVENTION

Bioreactors, also referred to as fermentors, are a part of biotechnological apparatuses. They have a closed reaction chamber, in which eukaryotic or prokaryotic cells are cultivated under conditions that are as optimal, defined and controlled as possible. Conversions of substances, mostly automated and controlled by process engineering, are researched, optimised and performed using the boundary conditions necessary for the organism and in the presence of the primary and secondary substances required for the process.

Biotechnological cultivation is carried out under conditions that are optimised for the organism and for the conversions to be achieved. For a large proportion of the cell types used, this process takes place at 37° C., at which temperature dry air can absorb around 40 grams of water per kilogram of air. This means that water is continuously withdrawn from the system when the culture is gassed with the gas composition required for the microorganisms. In order to counteract this effect, the exhaust gas stream is guided through the exhaust gas conduit provided with the temperature control device which cools the surface of the exhaust gas conduit, which then cools the gas stream, for example to a temperature between about 4° C. and about 10° C. By this means, the exhaust gas stream is cooled down significantly. The temperature on the surface of the exhaust gas conduit falls below the dew point. As a result of this measure, the water being removed in the exhaust gas stream condenses on the walls of the exhaust gas cooler and runs back into the culture medium.

When using such bioreactors in the field of cell culture technology, cultivation times ranging from a number of days to a few weeks are not atypical. The gassing rates are also significantly lower than in microbiological applications. For this reason, it may also be necessary to heat the exhaust gas stream in order to prevent clogging of the sterile filter connected downstream from the exhaust gas conduits.

Controlling the temperature by means of the temperature control device is typically done using a temperature control fluid. This fluid is conditioned in a separate unit. Mains water may also be used as an alternative if its temperature is sufficiently controlled.

When using coolants and separate units, complex connection technology is needed. The different temperatures of the surroundings and the connector units result in many temperature divergences, which is why strong formation of condensate on supply and discharge pipelines can be observed.

In typical biotechnological methods carried out on "benchtop scale" (laboratory scale), glass reaction vessels are frequently used. This allows an autoclavable bioreactor to be designed in which the glass reactor vessel can be steam sterilised in one piece in an autoclave. In this context, it is then necessary that all connections to the reaction vessel be disconnected from the control units before autoclaving. Connections are typically in the form of hose connectors such as clamp screw connections, push-in connectors, crimp connections and the like. Such an autoclavable design of the bioreactor thus requires that functional components of the biotechnological apparatus which connect to the bioreactor itself are mounted on the reactor vessel as efficiently as possible and can be dismantled again when autoclaving is due.

Another bioreactor design takes the form of single-use bioreactors, in which the reactor vessel, for example, is used in one cultivation process only, whereas functional elements assigned to the reactor vessel, such as stirrer drives, or the temperature control unit for exhaust gas removal, can be reused. In this connection also, it is necessary that functional components of the biotechnological apparatus which are coupled to the bioreactor be mounted on the reactor vessel and dismantled again after use as efficiently as possible.

Bioreactors, which are also frequently referred to as fermenters, enclose a reaction chamber in which biological or biotechnological processes can be carried out on a laboratory scale. Such processes include, for example, the cultivation of cells, microorganisms or small plants under defined, preferably optimized, controlled and reproducible conditions. Bioreactors mostly have a plurality of connectors via which the primary and secondary substances, as well as various instruments, such as sensors, can be introduced to the reaction chamber, or to which fluid conduits, for example, can be connected. Fluids, in particular gases, can be supplied to or removed from the reaction chamber through such fluid conduits, in particular gas conduits. Depending on the direction of fluid flow, fluid conduits can be referred to as feed conduits or discharge conduits. Gas conduits, for example, can be referred to as gas feed or gassing lines or conduits or as gas exhaust or discharge conduits, depending on the direction of the gas stream.

Bioreactors are preferably used in bioreactor systems, preferably in parallel bioreactor systems, not only in the field of cell cultivation but also in microbiological applications. Parallel bioreactor systems are described in DE 10 2011 054 363.5 and DE 10 2011 054 365.1, for example. In such a bioreactor system, a plurality of bioreactors can be operated in parallel and controlled with higher precision. High-throughput experiments that are well reproducible and scalable can be carried out in the individual bioreactors, even with small operating volumes.

In the cell culture field, such parallel bioreactor systems are used, for example, for test series for process optimization based on statistical planning methods (design of experiments DoE), for process development and in research and development, for example to cultivate different cell lines such as Chinese hamster ovary (CHO), hybridoma or NSO cell lines. In the context of the present application, the expression "cell culture" is specifically understood to mean the cultivation of animal or plant cells in a nutrient medium outside the organism.

In the field of microbiology, parallel bioreactor systems are likewise used for test series for process optimization based on statistical planning methods (design of experiments DoE), for process engineering and in research and development, for example to cultivate various microorganisms, in particular bacteria or fungi, such as yeast.

Bioreactors used in laboratories are often made of glass and/or metal, in particular of stainless steel, as the bioreactors must be sterilized between different uses, preferably by steam sterilization in autoclaves. Sterilizing and cleaning reusable bioreactors is a complex process. The sterilization and cleaning process can be subject to validation, and needs to be precisely documented for each individual bioreactor. Residues in a bioreactor which has not been fully sterilized can falsify the results of a subsequent process, or render them useless, and may cause disruption of the subsequent process. Furthermore, the sterilization process may also expose individual components or materials in bioreactors to stress and strain, and in some cases can damage them.

Single-use bioreactors provide an alternative to reusable bioreactors and are used to carry out just one biological or biotechnological process before being disposed of. By providing a new single-use bioreactor for each process, and one that is preferably sterilized during the production process, it is possible to reduce the risk of (cross-) contamination, while simultaneously obviating the need to perform and document the impeccable cleaning and sterilization of a previously used bioreactor. Single-use bioreactors are often designed as flexible containers, for example as bags, or as containers having walls that are flexible in sections thereof at least. Examples of such bioreactors are described in US 2011/0003374 A1, US2011/0058447A1, DE 20 2007 005 868U1, US 2011/0058448A1, US2011/0207218A1, WO 2008/088379A2, US 2012/0003733 A1, WO2011/079180A1, US2007/0253288A1, US 2009/0275121A1 and US 2010/0028990A1. Dimensionally stable single-use bioreactors are known from EP 2 251 407 A1 and from US 2009/0311776 A1, for example.

A sterile single-use bioreactor generally includes a fluid conduit attached thereto, which is likewise sterilized and provided for single use, in particular one or more gas conduits. Such a single-use fluid conduit may be embodied as a rigid pipe or as a flexible tube. A sterile filter which in most cases is likewise sterilized and provided for a single use is usually provided on a single-use fluid conduit, preferably at the end which is not attached to the bioreactor. In a gas conduit in particular, a sterile filter is used to filter gas flowing into a bioreactor through a gassing conduit, or gas flowing out of a bioreactor via an exhaust gas conduit.

When using bioreactors in biological or biotechnological processes, for example to cultivate various microorganisms, in particular bacteria or fungi, such as yeast, or for cultivating various cell lines such as Chinese hamster ovary (CHO), hybridoma or NSO cell lines, it is important that the sterility of the single-use bioreactor and its components is not compromised. In the context of the present application, the expression "cell culture" is specifically understood to mean the cultivation of animal or plant cells in a nutrient medium outside the organism.

Such biological and biotechnological processes are generally carried out under sterile conditions in aqueous media, also referred to as culture broths, in a reaction chamber of a bioreactor. Gaseous fluid, for example mixtures of nitrogen, oxygen, carbon dioxide, etc. are fed to the system during at least a certain period of cultivation in order to keep the biological processes running, and/or gaseous fluids such as methane, carbon dioxide, etc. are removed from the system that may also contain other components produced by biological processes. The sterile conditions in the reaction chamber of a bioreactor and hence also of the biological system, both when supplying fluids and also when removing fluids, are generally maintained by sterile filters inserted into the fluid stream. The gaseous fluid which is removed is typically saturated with water vapor. The temperature of the aqueous culture broth is mostly higher than the temperature of the system's environment, for example in a laboratory. In such cases, the removed gaseous fluid is cooled at least slightly when discharged from the reaction chamber of the bioreactor into the exhaust gas tube. This causes part of the water vapor in the gas to condense. It is desirable to return the condensate to the reaction chamber, because otherwise the concentration of media components in the culture broth could increase in the course of the process, which can lead, for example, to an undesirable increase in osmolality. Another disadvantage is that the sterile filter may be blocked by the formation of condensate, as a result of which the gaseous fluid can no longer be removed, thus causing the exhaust gas stream to be blocked. This can lead to the gas supply into the reaction chamber being blocked as well, thus disrupting or terminating the cultivation process.

Cooling devices are therefore deployed in the exhaust gas conduits in reusable bioreactors, as shown, for example, in US 2012/0103579 A1, US 2010/0170400 A1 and US 2011/0076759 A1. An exhaust gas cooling device for single-use bioreactors is proposed in WO 2011/041508 A1, for example.

Due to the need to preserve sterility, in particular, the use of systems for cooling exhaust gas has not yet become established practice in single-use bioreactors, however, which can lead to the aforementioned disadvantages of water extraction and filter blocking. In some existing solutions, the attempt is made to prevent blocking of a sterile filter by lowering the relative moisture in the exhaust gas stream to such an extent, by heating the exhaust gas in the region of the exhaust gas tube, that the exhaust gas can pass through the sterile filter without condensate being produced. This does not do away with the disadvantage that no condensate is recovered from the exhaust gas that could be returned to the culture solution. Moreover, blocking of the sterile filter can still occur when these solutions are applied. In order to increase process reliability, complex single-use sterile filters such as depth filters or capsule filters are often used, therefore, instead of membrane filters, which are inexpensive but have a tendency to clog. However, this results in higher costs for single-use bioreactors.

It is also tried to avoid blocking of the sterile filter by means of heating the sterile filter itself, by increasing the temperature in the sterile filter to avoid or reduce the forming of condensate. This also, inter alia, has the disadvantage that no condensate is recovered from the exhaust gas that could be returned to the culture solution, and also this approach cannot reliably enough prevent a blocking of the sterile filter.

A biotechnological device with a temperature control device is known from the patent application DE 10 2011 054 364.3. Although the biotechnological device described therein and the temperature control device likewise described therein provide advantages for bioreactors which can be autoclaved, it is nonetheless desirable to further simplify and improve temperature control of exhaust gases for sterile, single-use bioreactors, particularly with regard to process reliability and energy efficiency. The sterility of a single-use bioreactor and of a sterile disposable exhaust gas tube attached thereto should not be adversely affected by providing a device for controlling the temperature of the exhaust gas.

Another disadvantage of prior art solutions is that the temperature in the reaction chamber can be influenced or changed by feeding fluids or gases, for example cooled fluids, into the reaction chamber, which can have negative effects on temperature-sensitive processes especially, and may make it more complex or expensive to control the temperature of the culture broth. Also, the temperature control can be negatively influenced by feeding fluids or gases, for example cooled fluids, into the reaction chamber, particularly by cold gas impulses. Gas supply or gassing conduits may likewise be fitted with filters that may become blocked as a result of condensate forming. When feeding moist gas or gas mixtures, for example when feeding the exhaust gas from an upstream process as a feed gas to a downstream bioreactor, it may be desirable to filter out gas components by means of a filter, for which blocking of the filter is likewise disadvantageous.

SUMMARY OF THE INVENTION

The object of the invention is to specify improved technologies for controlling the temperature of an exhaust gas stream in a biotechnological apparatus comprising a bioreactor, and which make it easier to handle and operate such an apparatus.

It is a further object of the present invention to improve the fluid temperature control of inflowing or outflowing fluids, in particular gases, in a sterile single-use fluid conduit, in particular of exhaust gas in a sterile single-use gas conduit, of a single-use bioreactor, in order to prevent or mitigate one or more of the aforementioned disadvantages. An object of the present invention, particularly, is to specify a connection device for a sterile single-use fluid conduit of a single-use bioreactor, which improves the process reliability and/or the energy efficiency of fluid temperature control, in particular the temperature control of exhaust gas. Another object of the present invention is to provide a connection device for a sterile single-use fluid conduit of a single-use bioreactor, which facilitates the application of fluid temperature control. Yet another object of the present invention is to provide a connection device for a sterile single-use fluid conduit of a single-use bioreactor, which is inexpensive to produce and to use. Another object of the present invention is to specify a suitable method for treating a fluid stream, in particular a gas stream, in a biotechnological device.

This object is achieved, according to the invention, by a biotechnological apparatus comprising a bioreactor according to independent claim 1. An exhaust gas temperature control device for a bioreactor, according to independent claim 10, and a method for treating an exhaust gas stream in a biotechnological apparatus comprising a bioreactor, according to independent claim 11, are also specified. Advantageous embodiments of the invention are described in the dependent claims.

The invention includes the concept of a biotechnological apparatus comprising a bioreactor and an exhaust gas conduit designed and configured on the bioreactor, the removal of gases which are produced in a reactor vessel of the bioreactor during cultivation, and an exhaust gas temperature control device designed free of temperature control fluid, and a temperature control actuator, the exhaust gas temperature control device being arranged in releasable connection with the exhaust gas conduit with the aid of a connector device and thermally coupling the temperature control actuator to the exhaust gas conduit.

According to another aspect of the invention, an exhaust gas temperature control device for a bioreactor, designed free of temperature control fluid and having the following features is provided: a temperature control actuator designed free of temperature control fluid and configured to control the temperature of an exhaust gas conduit of a bioreactor, and a coupling mechanism assigned to a connector device, with which the temperature control actuator can be releasably mounted on the exhaust gas conduit and thermally coupled thereto.

The invention also includes a method for treating an exhaust gas stream in a biotechnological apparatus comprising a bioreactor, the method comprising the following steps: removing, via an exhaust gas conduit, a stream of gases produced during cultivation in a reactor vessel of the bioreactor, controlling the temperature of the exhaust gas stream in the exhaust gas conduit by means of an exhaust gas temperature control device designed free of temperature control fluid, in such a way that the exhaust gas stream condenses at least partially, and providing at least one part of the condensate formed when controlling the temperature of the exhaust gas stream for return to the cultivation process in the reactor vessel.

More specifically, the invention stipulates that the temperature of the exhaust gas stream produced during operation of the bioreactor be controlled by means of an exhaust gas temperature control device designed free of temperature control fluid, by providing a temperature control actuator free of temperature control fluid. In particular, the bioreactor may be an autoclavable bioreactor or a single-use bioreactor. The latter is preferably provided in sterile packaging. However, the proposed technologies can also be used in their various embodiments in hybrid variants of bioreactors.

The thermal actuator, which may also be referred to as the actuator, is thermally coupled by means of the connector device to the exhaust gas conduit and thus to the exhaust gas stream channelled therein, as a result of which an exhaust gas cooler is formed, for example. It is also possible, however, to use the temperature control device to supply heat, for example to heat a filter element in the exhaust gas stream. Coupling or arranging the exhaust gas temperature control device with the aid of the connector device automatically couples the temperature control actuator thermally to the exhaust gas conduit. In other words, whereas the temperature control actuator is thermally decoupled from the exhaust gas conduit when the exhaust gas temperature control device itself is not arranged on the exhaust gas conduit, thermal coupling between the temperature control actuator and the exhaust gas conduit is automatically established when the exhaust gas temperature control device is releasably mounted on the exhaust gas conduit with the aid of the connector device.

Designing the exhaust gas temperature control device free of temperature control fluid has the advantage over the prior art, which uses a fluid as the means for controlling the temperature of the exhaust gas, that pipelines and feed lines for the fluid can be dispensed with. Nor is there any need to connect or disconnect pipelines or connectors when disconnecting the functional components from the reactor vessel, and nor can condensate be formed in the pipelines and feed lines. The new technology does not require any additional, external device in order to provide and to process a temperature control fluid. This also does away with the energy consumption and the noise emission of the additional external device. Another advantage is that potential leakages, which can lead to the temperature control medium escaping and hence to damage being caused to parts of the system, are prevented in this manner.

Another advantage of the proposed technology is that the exhaust gas temperature control device can be detached from the bioreactor in a simple manner, for example when the latter is due to be treated in the autoclave, or a single-use reactor vessel is to be disconnected from the functional components coupled thereto, since there is no need to disconnect pipelines or feed lines that used in the prior art for operational management of the temperature control fluid. Furthermore, the proposed connector device automatically couples the temperature control actuator thermally to the exhaust gas conduit when the exhaust gas temperature control device is mounted. This also results in the exhaust gas conduit and the temperature control actuator being automatically thermally decoupled when the exhaust gas temperature control device is removed.

Surface contours which enlarge the thermal transfer surface when controlling the temperature of the exhaust gas stream may be formed in the exhaust gas channel in which the exhaust gas stream is guided in the exhaust gas conduit. Such surface contours may also be used additionally or alternatively to induce turbulence in the exhaust gas stream, which serves to improve heat transfer when controlling the temperature of the exhaust gas stream. The exhaust gas temperature control device may have one or more fans that are used for improving thermal coupling between the temperature control actuator and the operating environment. The operating environment may be the ambient air, for example, or some other fluid-free potential.

If temperature control results in at least partial condensing of the exhaust gas stream, it may be stipulated in one variant of the invention that the exhaust gas conduit be coupled to a fluid return line which is configured to return condensate formed when controlling the temperature at least partially to the cultivation process in the bioreactor.

In one preferred development of the invention, the exhaust gas temperature control device is mechanically coupled to the exhaust gas conduit by means of the connector device. The mechanical connection can generally be designed in a variety of ways that can also be combined with each other, including a plug or screw connection, for example. The mechanical coupling may be provided in elastic form, by producing an elastic connection, for example by using one or more elastic spring members and/or by using an elastic mounting for one or more coupled components, for example with the aid of an elastically yielding material such as rubber.

In one expedient configuration of the invention, the mechanical coupling of the exhaust gas temperature control device to the exhaust gas conduit is self-locking. Self-locking can be achieved, for example, by means of a press fit, as described in more detail below, since a press-fit connection also prevents any unintended detachment. The self-locking nature of the mechanical connection between the exhaust gas temperature control device and the exhaust gas conduit simultaneously establishes automatic thermal coupling between the temperature control actuator and the exhaust gas conduit, as a result of which the temperature control actuator then thermally couples to the exhaust gas stream.

In one advantageous embodiment of the invention, the mechanical coupling of the exhaust gas temperature control device is formed by means of a push-on connection which is embodied by mutually assigned guide members on the exhaust gas temperature control device and the exhaust gas conduit cooperating with each other in such a way when pushing on the exhaust gas temperature control device that a straight relative movement between exhaust gas temperature control device and the exhaust gas conduit is performed. For example, mutually engaging guide members may be provided which are preferably in positive engagement with each other, for example by using undercuts. In order to form a press fit in this embodiment of the invention, the guide members engaging with each other may have conical or wedge-shaped portions. The mutually assigned guide members of the push-on connection allow the exhaust gas temperature control device to be pushed onto exhaust gas conduit to produce the mechanical coupling with which the thermal coupling between the exhaust gas conduit and the temperature control actuator is also produced. In one configuration, the exhaust gas temperature control device is pushed onto the exhaust gas conduit in such a way that it is moved along an exhaust gas stream formed in the exhaust gas conduit. It may be stipulated, for example, that it is possible to remove the exhaust gas temperature control device in the axial direction of the bioreactor, which is appropriate, for example, when space is limited in the biotechnological apparatus. In this or other embodiments, the connection forming the mechanical and thermal coupling is conducive to compact system design.

In one development of the invention, the mechanical coupling of the exhaust gas temperature control device to the exhaust gas conduit may be formed with a press fit in such a way that mutually assigned thermal transfer surfaces on the exhaust gas temperature control device and on the exhaust gas conduit are pressed against each other. In this configuration, a press fit of the exhaust gas temperature control device onto the exhaust gas conduit is produced by means of the mechanical connection, in which mutually assigned heat-exchanging surfaces on the exhaust gas temperature control device and on the exhaust gas conduit are pressed against each other when in the coupled state, thus providing a press-fit connection.

In one development of the invention, the thermal coupling of the temperature control actuator to the exhaust gas conduit preferably includes the arrangement of a support surface which extends the thermal energy transfer surface on the exhaust gas conduit and an associated actuator temperature control surface, such that the flat surfaces touch each other. In one configuration, the support surface on the exhaust gas conduit extends along the exhaust gas channel formed therein. When the exhaust gas temperature control device is pushed onto the exhaust gas conduit, the two mutually assigned surfaces, i.e. the support surface on the exhaust gas conduit and the temperature control surface on the actuator, slide onto each other so that the overlapping area is progressively increased until an optimal overlap is reached when the exhaust gas temperature control device is pushed on fully. In this way, it is possible in one embodiment of the invention to produce a variant of the press-fit connection described above.

In one advantageous variant of the invention, the temperature control actuator may be coupled to a control unit which is configured to deactivate the temperature control actuator automatically when the exhaust gas temperature control device is disconnected from the exhaust gas conduit. Automatic deactivation of the temperature control actuator is realised with the aid of the control unit. The temperature control function is automatically deactivated, for example by interrupting the supply of energy and/or a signal feed to the temperature control actuator. In one configuration, one or more other functional components of the biotechnological apparatus, such as ventilation elements and/or components that produce a gas stream for the bioreactor, are automatically activated/deactivated in the same manner, in addition to the automatic deactivation and/or automatic activation of the temperature control actuator. The other functional components may be coupled to the same control unit. A further control unit may also be provided, which is then used for automatic activation/deactivation when the exhaust gas temperature control device is disconnected from the exhaust gas conduit.

In one development of the invention, the control unit may be designed with at least one deactivation mechanism selected from the following group of deactivation mechanisms: optical deactivation, mechanical deactivation, magnetic deactivation and electrical deactivation. The respective mechanism is formed by a sender-receiver sensor system appropriate to the respective design. The sensor member, which is disposed on the exhaust gas conduit remaining on the bioreactor, preferably works passively, i.e. in particular it does not require its own power supply. Examples of such sensor members are a permanent magnet in the mechanical deactivation mechanism, or a light reflection member in the case of an optical sensor. RFID (Radio Frequency Identification) technology may also be used in this context, which also allows electronically retrievable information to be stored in the RFID chip on the exhaust gas temperature control device. A single deactivation mechanism, or any combination of a plurality of deactivation mechanisms, may be used to implement the control unit that automatically deactivates the temperature control actuator and other functional components, selectively, when the exhaust gas temperature control device is disconnected from the exhaust gas conduit. Conversely, the mechanism used may also selectively induce automatic activation of the temperature control actuator and, selectively, of other functional components, in particular in such a way that the temperature control function of the temperature control actuator is provided after the exhaust gas temperature control device has been attached. The control unit may be provided with optical deactivation, for example, where deactivation occurs when signals from an assigned optical emitter no longer arrive at an optical receiver. As an alternative or in addition thereto, another of the aforementioned deactivation mechanism may be implemented in similar manner. In the case of magnetic deactivation, a Hall sensor may be used, for example, in which a permanent magnet is arranged as a sensor on the exhaust gas conduit, for example.

In one preferred development of the invention, the temperature control actuator has at least one Peltier element. In this or in other embodiments, the exhaust gas temperature control device may be provided with one or more heat sinks and/or at least one fan assembly, thus supporting an optimised configuration of the temperature control function.

In combination with the exhaust gas temperature control device and the method for treating an exhaust gas stream, the above descriptions apply accordingly in connection with advantageous configurations and variants.

According to another aspect of the invention, the objects are achieved by a reusable connection device for a sterile, single-use fluid conduit of a single-use bioreactor, the connection device comprising a receptacle in which a portion of a fluid conduit can be detachably arranged, and a coupling member having a coupling face for connecting the connection device to a temperature control device, wherein the receptacle has a contact surface which is arranged and adapted in such a way that the contact surface abuts a portion of a fluid conduit arranged in the receptacle, and wherein a portion of a fluid conduit can be introduced into the receptacle in a direction running substantially orthogonally to a longitudinal axis of the connection device.

What is particularly preferred is a reusable connection device for a sterile, single-use gas conduit of a single-use bioreactor, comprising a receptacle in which a portion of a gas conduit can be detachably arranged, and a coupling member having a coupling face for connecting the connection device to a temperature control device, wherein the receptacle has a contact surface which is arranged and adapted in such a way that the contact surface abuts a portion of a gas conduit arranged in the receptacle, and wherein a portion of a gas conduit can be introduced into the receptacle in a direction running substantially orthogonally to a longitudinal axis of the connection device.

In the present description, the embodiments and advantages of the invention are described for the gas conduction in particular, and also for the exhaust gas conduction in particular. However, the embodiments and advantages can also be realized for gas conduits with a different direction of flow, also and in particular for gassing or feed gas conduits. The embodiments and advantages described here can also be realized for fluid conduits in general.

The embodiments and advantages of the invention are likewise described with specific reference to controlling the temperature of an exhaust gas stream by means of a temperature control device. Here, too, the respective embodiments and advantages can also be realized with regard to temperature control of fluids, regardless of their direction of flow.

The invention is based on the finding that it is possible to avoid compromising the sterility of a single-use bioreactor and of a gas conduit connected thereto, and to obtain an inexpensive solution for controlling gas temperature, by using a prior art single-use bioreactor with a sterile, single-use gas conduit connected thereto and by arranging thereon a reusable connection device according to the invention. It is thus possible to use conventional single-use bioreactors, without increasing their production cost with special devices. At the same time, the reusability of the inventive connection device keeps the costs for gas temperature control low.

In order to achieve this, the connection device is provided with a receptacle in which a portion of the gas conduit, in particular a portion of an exhaust gas tube, can be detachably arranged. A relative movement between the gas conduit, in particular the exhaust gas tube, and the connection device is performed substantially orthogonally to a longitudinal axis of the connection device, i.e., the gas conduit can be inserted into the receptacle in a substantially radial direction (in relation to a conduit axis of a straight conduit). The longitudinal axis of the connection device is understood here to be an axis extending in the direction the connection device has its largest extension. The longitudinal axis of the connection device is preferably identical to, or parallel to a conduit axis of the gas conduit when the conduit is straight.

The gas conduit and the connection device are thus connected and disconnected in a simple manner. The connection device with receptacle is preferably attached to and detached from the gas conduit gradually, in a direction substantially orthogonal to the extension of the receptacle. This is particularly advantageous because such an arrangement ensures in a particularly simple way that the gas conduit does not have to be dismantled from the single-use bioreactor and that there is no need to dismantle the sterile filter from the gas conduit, thus ensuring that the system retains its sterility. Once a sterile single-use bioreactor has been provided, the connection device according to the invention can thus be arranged on the sterile single-use exhaust gas tube so that the process can be carried out, by inserting a portion of the gas conduit into the receptacle of the connection device, or by attaching the connection device with receptacle to the gas conduit. When the process has been completed, and before the single-use bioreactor is disposed of, the connection device can be removed again from the gas conduit and is available for re-use. The sterility of the single-use gas conduit or of the single-use bioreactor is not compromised by the connection device being detachably attached to them.

A fluid conduit, in particular a gas conduit, may be embodied, for example, as a flexible tube or as a dimensionally stable pipe.

In one embodiment as a flexible tube, it is particularly preferred that the connection device is embodied in a dimensionally stable form. When the gas conduit is embodied as a pipe, it is preferred that the connection device, in particular the receptacle and the contact surface, are made of a material which is deformable, and preferably elastically deformable. This combination allows the gas conduit and the connection device to be connected and disconnected in an advantageously simple manner, in that the gas conduit and/or the connection device in the aforementioned combination permit a certain degree of deformability, which then allows a press fit or a clamping fit, for example, to be easily established or released.

The connection device also has a coupling member with which the connection device can be attached to a temperature control device. By means of such a temperature control device, it is possible to control the temperature in a gas conduit, and thus also a gas stream flowing in the gas conduit. In contrast to the gas conduit being detachable arranged in the receptacle, the connection between the coupling member and a temperature control device may be detachable or permanent. The connection between the coupling member and a gas temperature control device is preferably a thermally coupling connection, in order to ensure good thermal conductivity between the connection device and the temperature control device. The coupling member has a coupling face which is preferably planar and which can be brought into planar contact with a temperature control surface of the temperature control device.

The receptacle of the connection device has a contact surface which abuts the outer surface of a portion of a gas conduit arranged in the receptacle. In the cross-section of the receptacle, the contact surface preferably forms a contact section which is substantially arcuate in shape. The contact surface results from the preferably arcuate profile of the contact section and a longitudinal extension of the receptacle in the direction of a longitudinal axis. The radius of the contact section of the receptacle in cross-section is preferably adapted to the radius of a gas conduit, in order to allow contact between the contact surface and a corresponding area on the outer surface of the gas conduit. The contact surface preferably lies over its entire surface against a corresponding area of the outer surface of the gas conduit. Such contact over the entire surface permits good heat transfer between the connection device and the gas conduit. This is advantageous for efficiently transmitting the temperature control capacity, in particular the cooling capacity, of a gas temperature control device connected to the coupling member, to the gas conduit and to a gas stream flowing therein.

The connection device also has the advantage that it stabilizes the portion of the gas conduit arranged in the receptacle, thus preventing any kinking of the gas conduit, in particular when the latter is embodied as a flexible tube. This stabilization, in particular when it is performed in a respective direction, can also foster the return flow, under the force of gravity, of condensate which is formed in the gas conduit into the single-use bioreactor.

Another advantage of the connection device according to the invention is that it broadens the range of applications for single-use bioreactors to sterile applications in which efficient recovery of fluids from exhaust gas is obligatory.

It is particularly preferred that the connection device according to the invention be used with a single-use bioreactor such as the one described in the applicant's application EP12172304.3 entitled "Single-use bioreactor and head plate, and a process of manufacturing same".

The receptacle may have a first and a second part, the two parts being designed to be joined together in a direction running substantially orthogonally to a longitudinal axis of the connection device and to receive a portion of a fluid conduit, in particular of a gas conduit, in the receptacle. In this embodiment also, the gas conduit is arranged in the receptacle in a substantially radial direction relative to an axis of the gas conduit, as a result of which the sterility of the systems is similarly preserved in advantageous manner, in particular by avoiding any separation of the gas conduit and the sterile filter, or from the gas conduit and the single-use bioreactor.

In one preferred embodiment, the receptacle is designed in such a way that a portion of a fluid conduit, in particular a portion of a gas conduit, can be held therein clampingly and/or by form-locking effect. A particular good thermal coupling, and therefore particularly good thermal transmission can be achieved by virtue of these options for establishing a connection between the receptacle and the fluid or gas conduit.

It is particularly preferred that a flexible tube is elastically deformed when inserted into the receptacle and that a respective area of the outer surface of the tube then comes into contact with the contact surface of the receptacle when the deformed tube regains its shape in the receptacle.

An alternative preferred embodiment is one in which the receptacle is elastically deformed when the receptacle of the connection device is attached to a dimensionally stable pipe, and the contact surface of the receptacle wraps itself around a respective area on the outer surface of the pipe.

It is particularly preferred that the connection device is made of a material having a high thermal conductivity, or includes such a material. A thermal conductivity: $\lambda$, of more than 10 W/(m*K) is preferred. A thermal conductivity: $\lambda$, of more than 15 W/(m*K) is particularly preferred, in particular a thermal conductivity of more than 25 W/(m*K), more than 50 W/(m*K), more than 75 W/(m*K), more than 100 W/(m*K), more than 150 W/(m*K) or more than 200 W/(m*K). It is particularly preferred that the connection device is made of aluminum or includes aluminum. Other preferred materials for the connection device are metals such as stainless steel, or other materials with high thermal conductivity. Composite materials comprising a plastic matrix and a highly thermally conductive material embedded therein can also be used, for example, particularly when it is preferred that the connection device is elastically deformable.

It is also preferred that the connection device has a longitudinal extension which is shorter than an extension of a fluid conduit between a connection of the fluid conduit to a single-use bioreactor and to a sterile filter arranged on the fluid conduit. More specifically, it is preferred that the connection device has a longitudinal extension which is shorter than an extension of a gas conduit between a connection of the gas conduit to a single-use bioreactor and to a sterile filter arranged on the gas conduit.

In this way, it is possible to ensure that the connection device is not longer than the portion of the gas conduit which is available for connection purposes. However, it is also preferred that the longitudinal extension of the connection device accounts for a large proportion of the length of the gas conduit between its respective connections to the single-use bioreactor and to a sterile filter, since it is possible in this way to increase the contact surface available for heat transfer.

The receptacle and the contact surface preferably have the same longitudinal extension, that is to say, the preferably substantially arcuate contact section in the cross-section of the receptacle is preferably embodied over the entire length of the receptacle.

It is further preferred that the connection device has a connecting section with which the connection device can be detachably attached to a connection member of a single-use bioreactor. This attachment is preferably a detachable plug connection, the connecting section of the connection device preferably being insertable into a respective connection member of the single-use bioreactor. The connection member may be arranged on a head plate of a single-use bioreactor, for example.

By connecting the connection device via a connecting section to a connection member of the single-use bioreactor, the connection device with the gas conduit, in particular a flexible tube, detachably place therein can be stabilized, preferably in a position which makes it easier for the condensate formed in the gas conduit to flow back into the reaction chamber of the single-use bioreactor under the force of gravity.

The connection device preferably has a thermal insulation member also, which is detachably connected to the connection device. This thermal insulation member is used to insulate the gas conduit and also, if applicable, the connection device surround said gas conduit. Thermally insulating the gas stream serves specifically to prevent or reduce condensate forming on the outside of the gas conduit or the connection device.

The thermal insulation member may preferably be connected by form-locking effect and/or by clamping to a portion of the gas conduit and/or of the connection device. The thermal insulation member is preferably attached detachably to the gas conduit and/or to the connection device and is designed to be reusable. The connection may be established by the thermal insulation member being elastically deformable, at least within limits, and being arranged on one portion of the gas conduit and/or of the connection device through a respective deformation, for example widening, and that a clamping connection and/or a form-locking connection is realized when the elastically deformable member is restored to its original shape.

The thermal insulation member may be embodied in two parts that are preferably joined together in a direction which is substantially orthogonal to a longitudinal axis of the thermal insulation member that is preferably identical or parallel to a longitudinal axis of the connection device, thus surrounding a portion of the gas conduit and/or a part of the connection device.

The thermal insulation member may preferably include or consist of materials with poor thermal conductivities and preferably having embedded insulated cavities, such as foamed polymers.

According to yet another aspect of the invention, the objects of the invention are achieved by a reusable temperature control device for controlling the temperature of a sterile single-use fluid conduit, in particular of a sterile single-use gas conduit, of a single-use bioreactor, the temperature control device comprising a temperature control actuator which does not contain any temperature control fluid, and which is characterized by a connection device as described in the foregoing for connecting the temperature control device to a fluid conduit, in particular to a gas conduit, of a single-use bioreactor.

It is particularly preferred that the temperature control actuator can be mounted on the coupling member of the connection device, preferably in a thermally coupling manner. Another particularly preferred embodiment is one in which the temperature control actuator can be detachably mounted on the coupling member of the connection device. Such a detachable connection may be a form-locking and/or force-locking connection, for example, and may be embodied as a plug connection, a snap-on connection, a screw connection or a sliding connection. As an alternative, the temperature control actuator may be connected in such a way to the coupling member that it is not possible for a user to dismantle it. This may be realized as an inseparable, integral connection between the temperature control actuator and the connection device, or by some other, basically detachable connection that is not accessible or detachable for a user, however, when the device is used in the intended manner.

In one preferred embodiment, the temperature control device is characterized by at least one heat transmission member for controlling the temperature of, in particular for heating, a sterile filter of a single-use bioreactor, wherein the at least one heat transmission member is connected thermocouplingly to the temperature control actuator. It is particularly preferred that waste heat from the temperature control actuator is used to heat the at least one heat transmission member.

This has the advantage that any waste heat arising when exhaust gas is cooled to recover condensate is not simply dissipated, but is used to heat the sterile filter. The process reliability can be further enhanced by this combination, since cooling of the exhaust gas causes not only condensate to form, thus reducing the moisture content of the exhaust gas, but also prevents, due to the sterile filter being heated simultaneously, any water vapor remaining in the exhaust gas from blocking the sterile filter. An energy-efficient solution is simultaneously created in this way, in which the waste heat generated by the cooling process is used to heat the heat transmission member. The heat transmission member and the temperature control actuator, preferably the warm side of the temperature control actuator, are preferably coupled thermally via a heat-conductive heat transmission body which can also be referred to as a heat sink, since its primary function is to conduct the waste heat away from the temperature control actuator. The heat sink may be a continuous component that connects the temperature control actuator to the heat transmission member.

In another preferred embodiment, the temperature control device is characterized by a second heat transmission member for controlling the temperature of, in particular for heating a sterile filter of a single-use bioreactor, the second heat transmission member being connected thermocouplingly to the temperature control actuator, the first and second heat transmission member preferably being adapted and arranged in such a way that they can at least partially enclose a sterile filter.

It is particularly preferred that waste heat from the temperature control actuator is used to heat the second heat transmission member.

This configuration further increases not only the process reliability but also the energy efficiency. The arrangement of two heat transmission members on preferably two different sides of the sterile filter results in improved, more uniform heating of the sterile filter.

The first and/or second heat transmission members may preferably be embodied in plate-shaped form, if necessary with a slot for a gas conduit to pass through. Further the first and/or second heat transmission members preferably comprise on their respective sides facing the sterile filter an indentation for receiving at least a part of the sterile filter, wherein the indentation preferably is formed as a counterpart to the part of the sterile filter to be received therein. This has the advantage that a better form-locking effect of the first and/or second heat transmission members and the sterile filter is achieved and thus a better heat transfer can be realized.

It is also preferable that the first and/or second heat transmission members are mounted pivotably about a horizontal axis in order to make it easier to enclose and release the sterile filter. This pivotable mounting of the first and/or second heat transmission members is preferably done on a heat transmission body which connects the heat transmission members to the temperature control actuator.

It is particularly preferred that the temperature control device is embodies as an exhaust gas temperature control device which does not contain any temperature control fluid, as described in DE 10 2011 054 364.3. More specifically, it is preferred that single ones or several of the embodiments of the exhaust gas temperature control device described in DE 10 2011 054 364.3 can be combined with single ones or with several of the previously described embodiments of the connection device.

According to another aspect of the invention, the objects of the invention are achieved by a biotechnological device comprising a single-use bioreactor provided with a sterile single-use fluid conduit, in particular gas conduit, and a reusable temperature control device as described in the foregoing, and/or a reusable connection device as described in the foregoing.

It is particularly preferred that the biotechnological device is embodied as biotechnological device of the kind described in DE 10 2011 054 364.3. More specifically, it is preferred that single ones or several of the embodiments of the biotechnological device described in DE 10 2011 054 364.3 can be combined with single ones or with several of the previously described embodiments of the connection device or of the temperature control device.

It is also preferred that the single-use bioreactor is embodied as a single-use bioreactor such as the one described in the applicant's application EP12172304.3 entitled "Single-use bioreactor and head plate, and a process of manufacturing same". More specifically, it is preferred that single ones or several of the embodiments of the single-use bioreactor device described therein can be combined with single ones or with several of the previously described embodiments of the connection device or of the temperature control device.

According to another aspect of the invention, the objects of the invention are achieved by a method for treating a fluid stream in a biotechnological device, comprising the steps of supplying or discharging a fluid stream from a or into a single-use bioreactor via a sterile single-use fluid conduit, and arranging a reusable connection device as previously described on a portion of a fluid conduit. What is particularly preferred is a method for treating a gas stream in a biotechnological device, comprising the steps of supplying or discharging a gas stream from a single-use bioreactor via a sterile single-use gas conduit, and arranging a reusable connection device as previously described on a portion of a gas conduit.

The method can preferably be developed by the steps of connecting a reusable temperature control device to the coupling member of the connection device, controlling the temperature of a fluid stream in a fluid conduit by means of the temperature control device in such a way that the fluid stream is at least partially condensed, and providing at least one part of the condensate formed when controlling the temperature of the fluid stream for return to a single-use bioreactor. Particular preference is given to a development of the method comprising the steps of connecting a reusable temperature control device to the coupling member of the connection device, controlling the temperature of a gas stream in a gas conduit by means of the temperature control device in such a way that the gas stream is at least partially condensed, and providing at least one part of the condensate formed when controlling the temperature of the gas stream for return to a single-use bioreactor.

With regard to the advantages, variants of the invention and details of the method and developments thereof, reference is made to the above description of the respective device features.

According to a further aspect of the invention, the objects of the invention are achieved by using a reusable connection device as previously described in order to connect, preferably with thermal coupling, a portion of a sterile single-use fluid conduit, a portion of a sterile, in particular single-use gas conduit of a single-use bioreactor, to a temperature control device.

DESCRIPTION OF PREFERRED
EMBODIMENTS OF THE INVENTION

Figure 2:
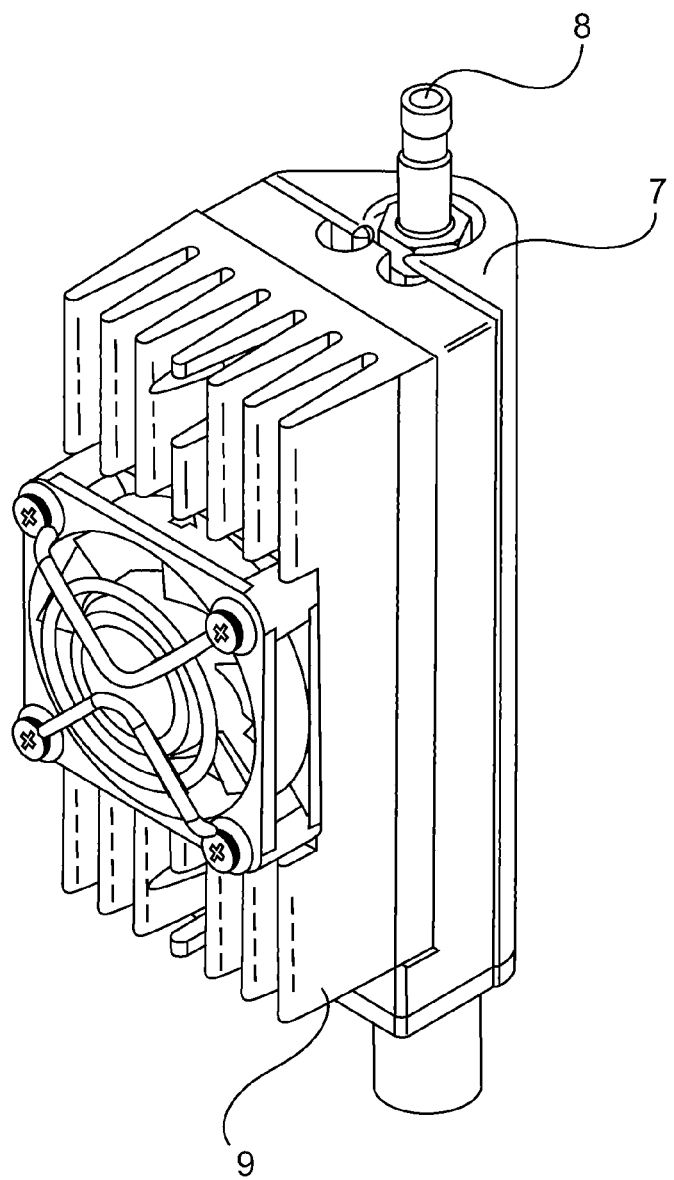
Figure 3:
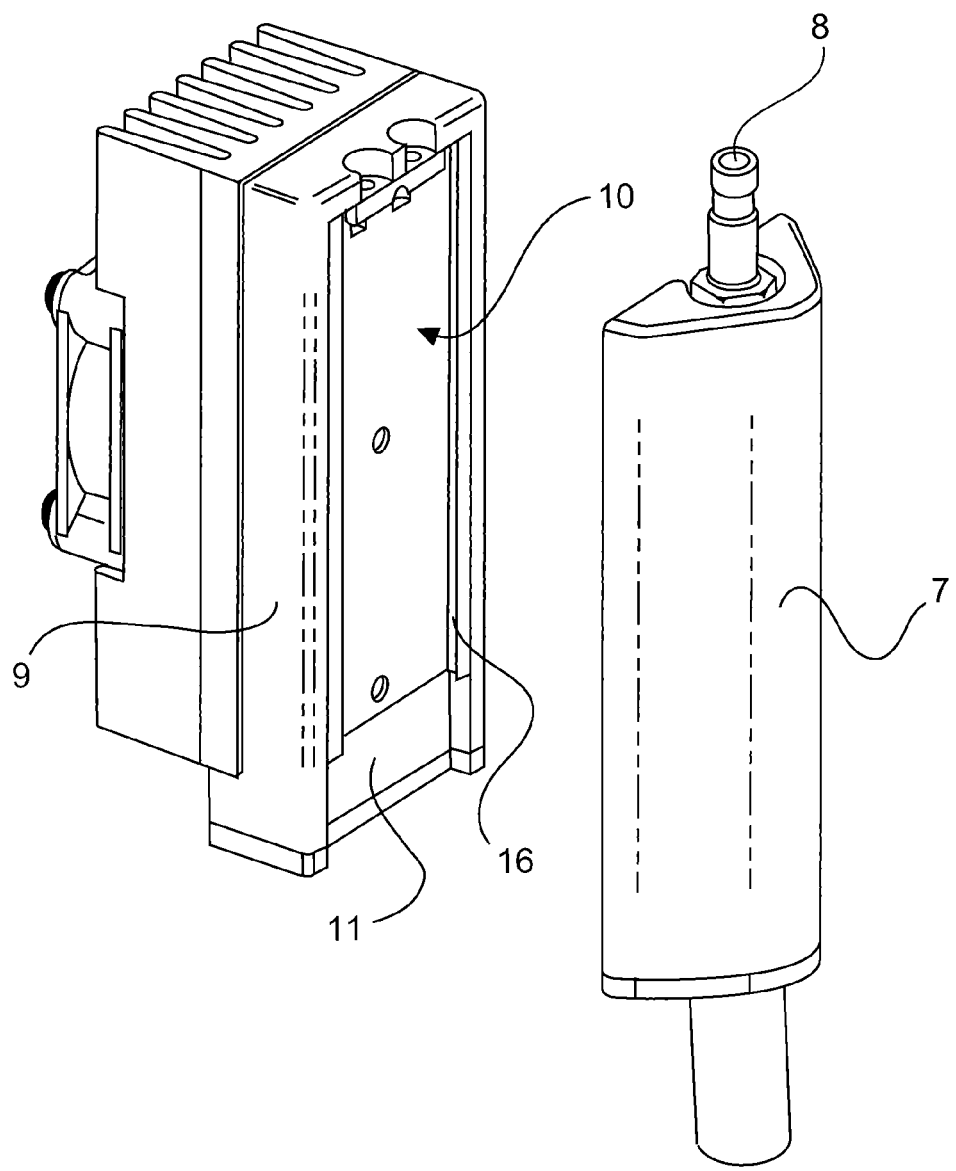
Figure 4:
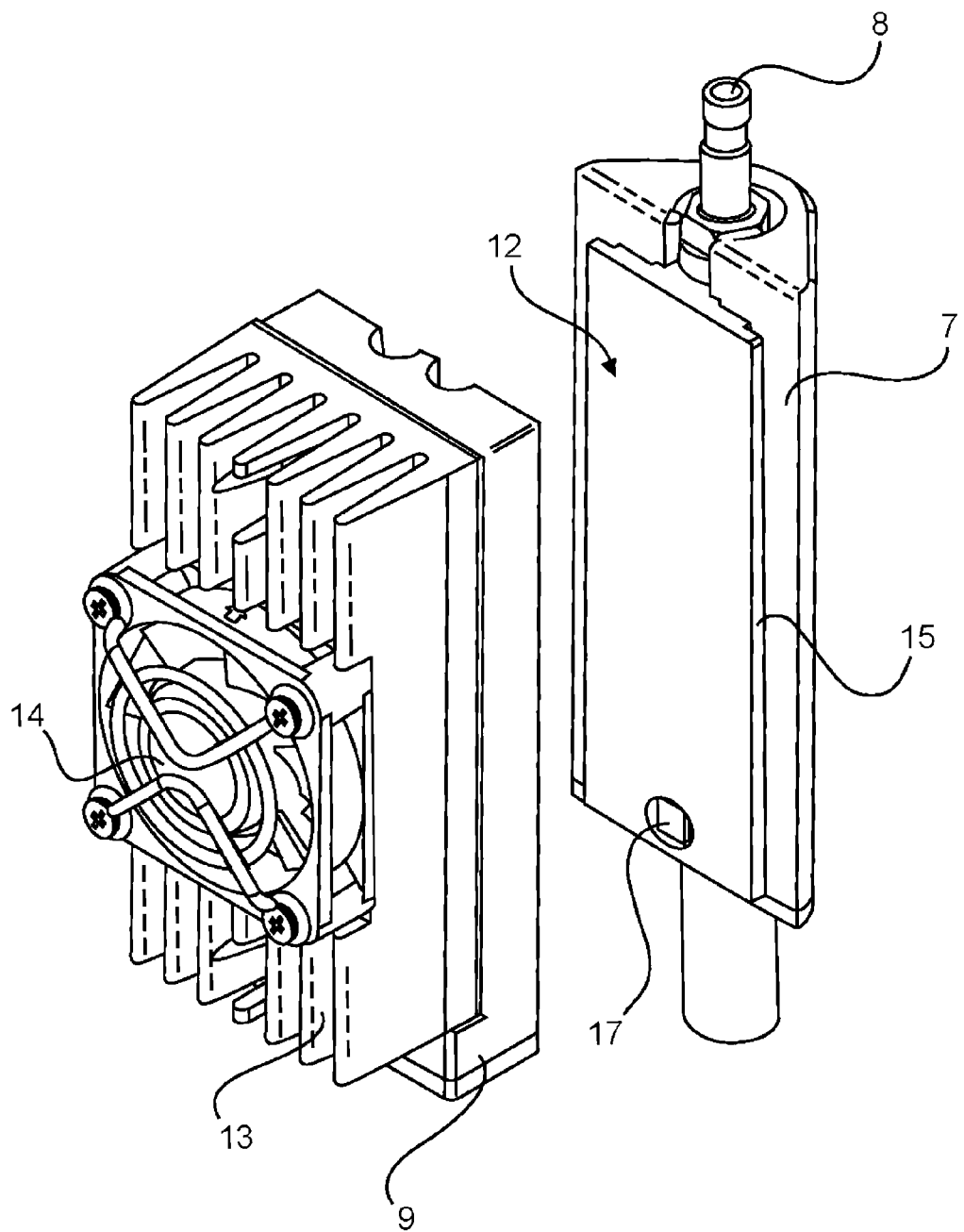
Figure 5:
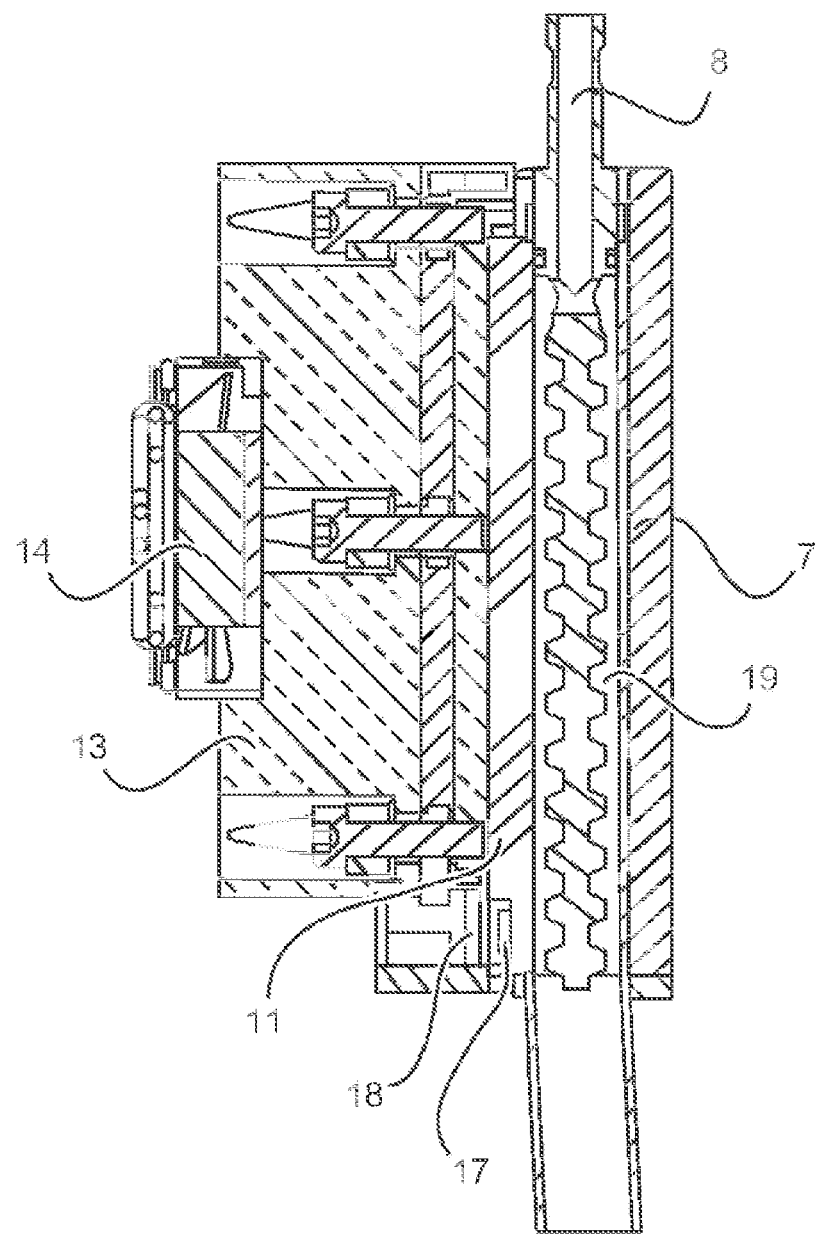
Figure 6A:
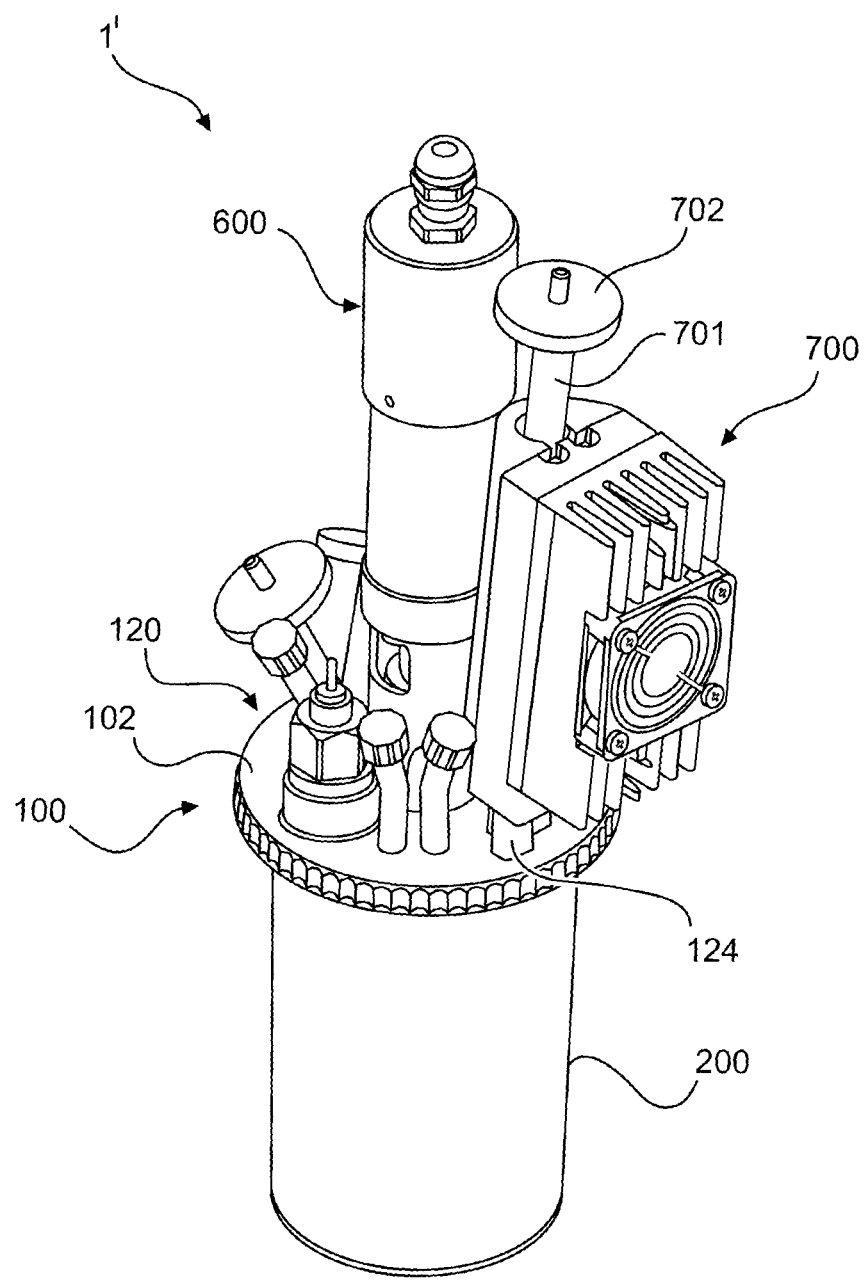
Figure 6B:
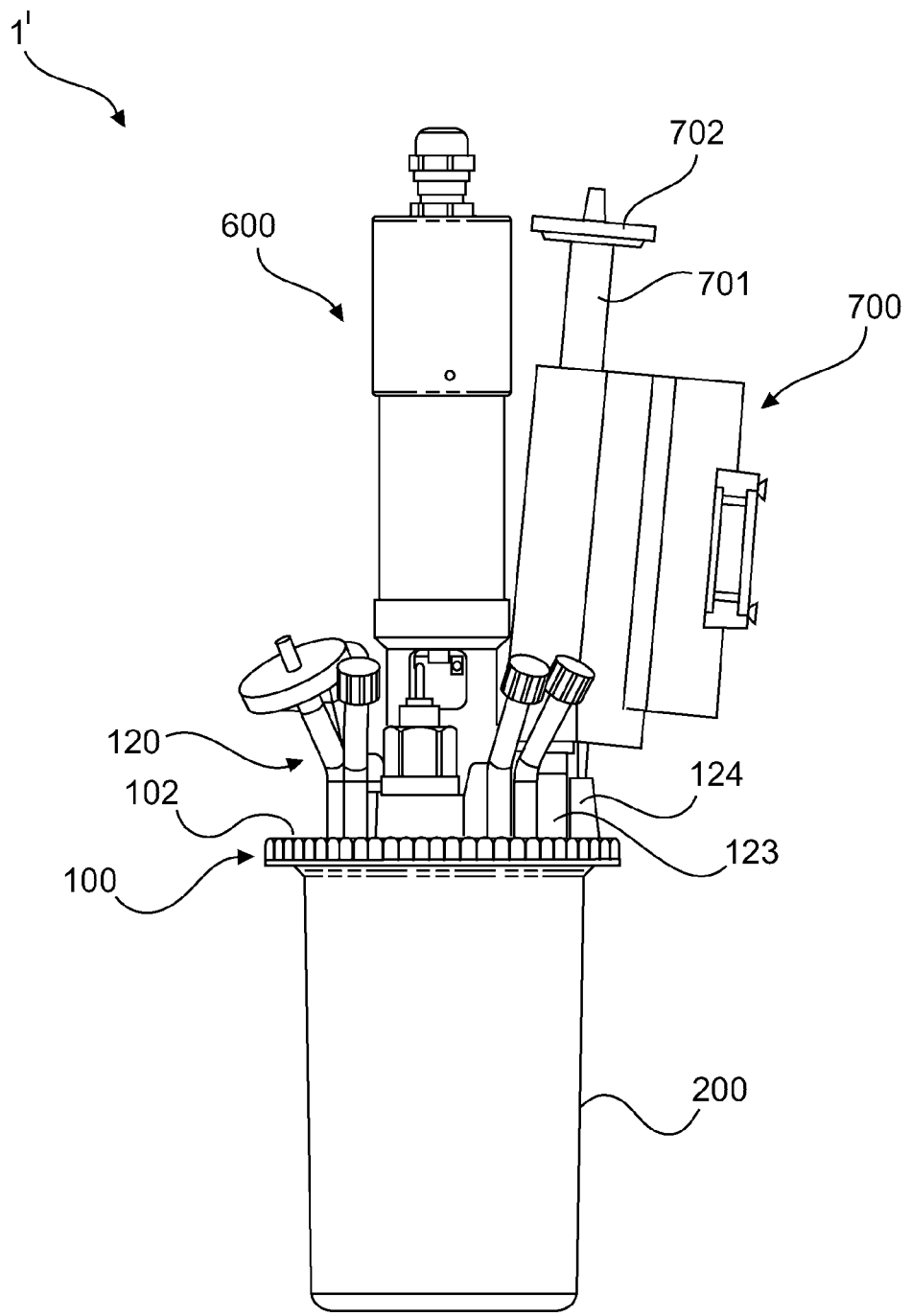
Figure 6C:
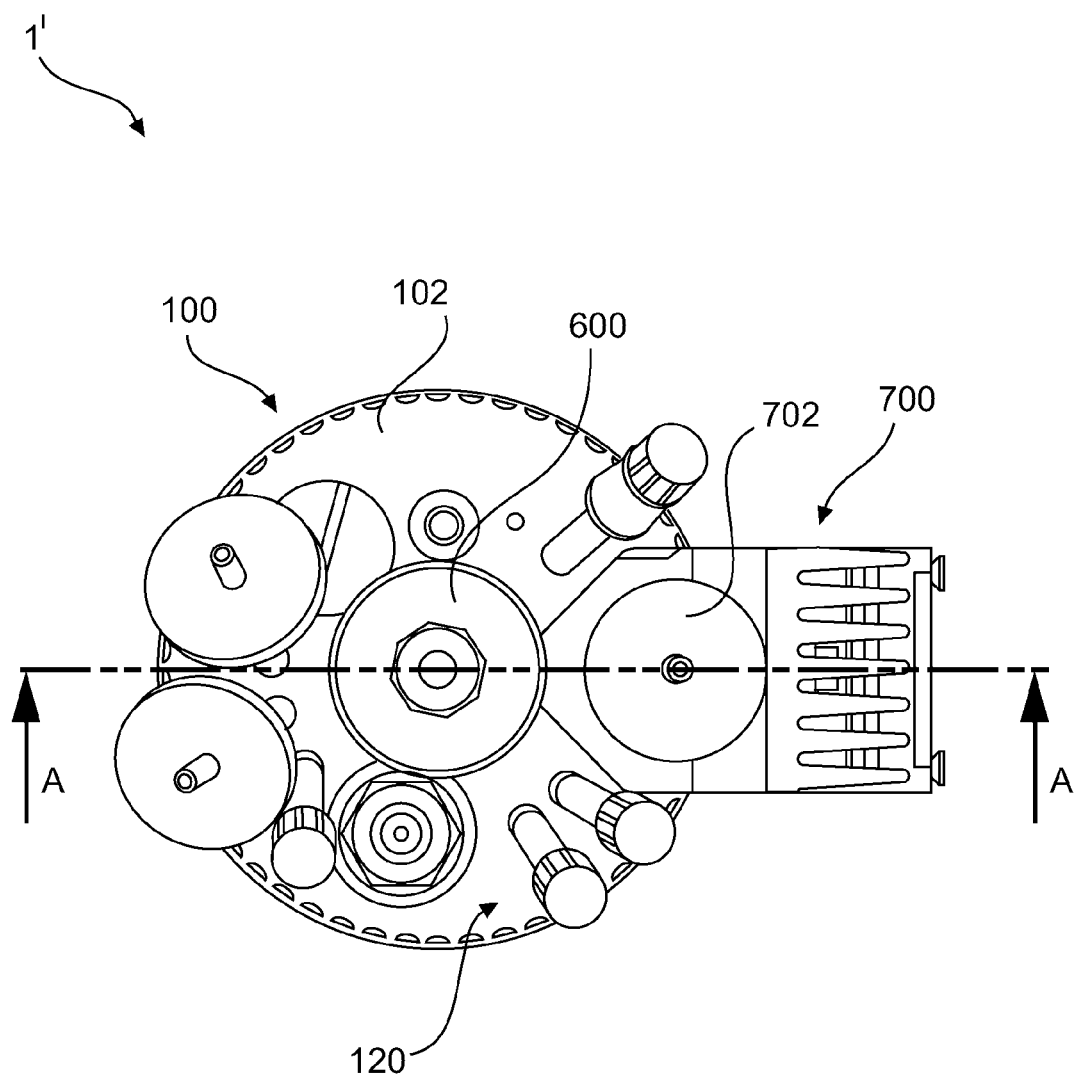
Figure 6D:
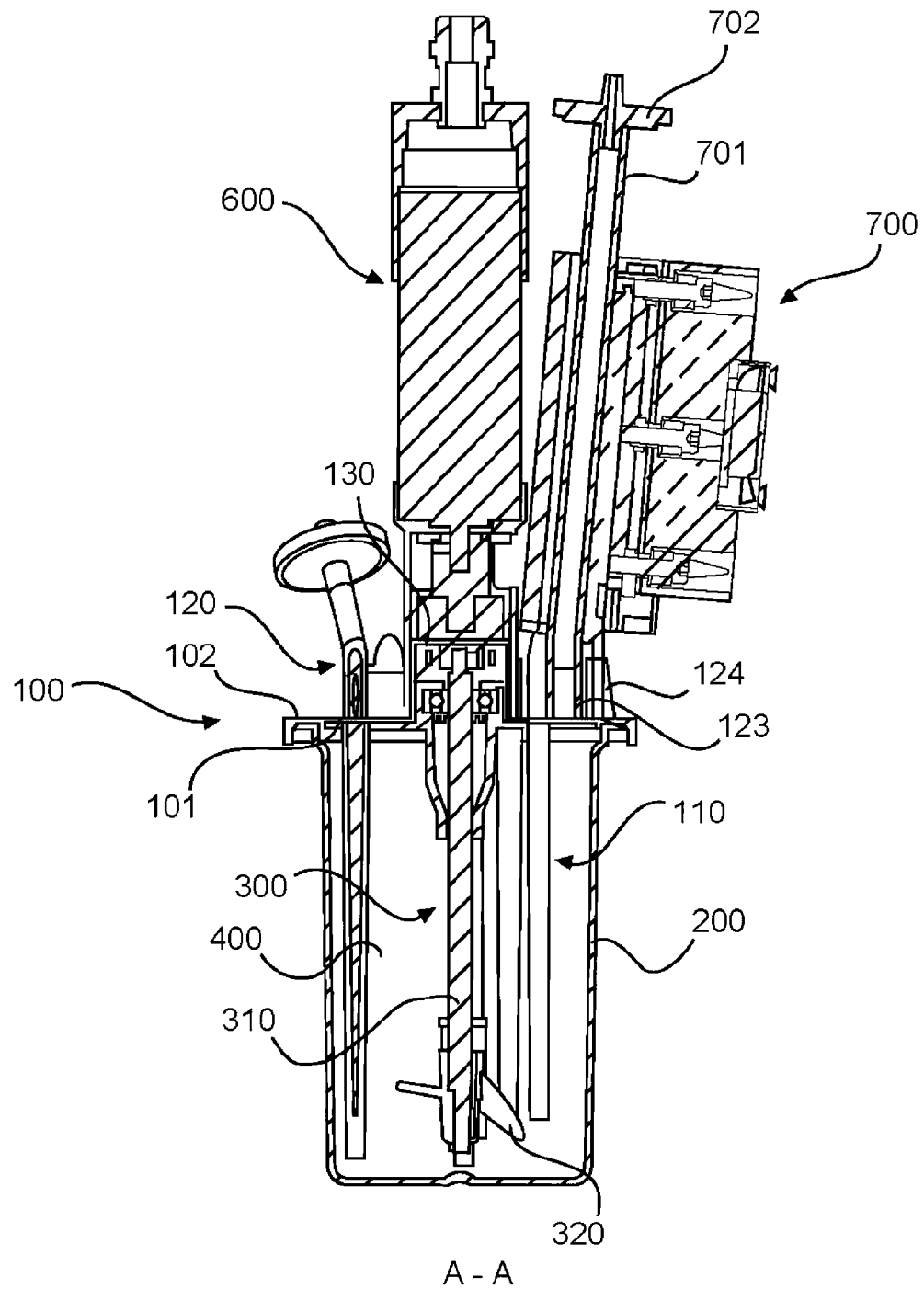
Figure 7:
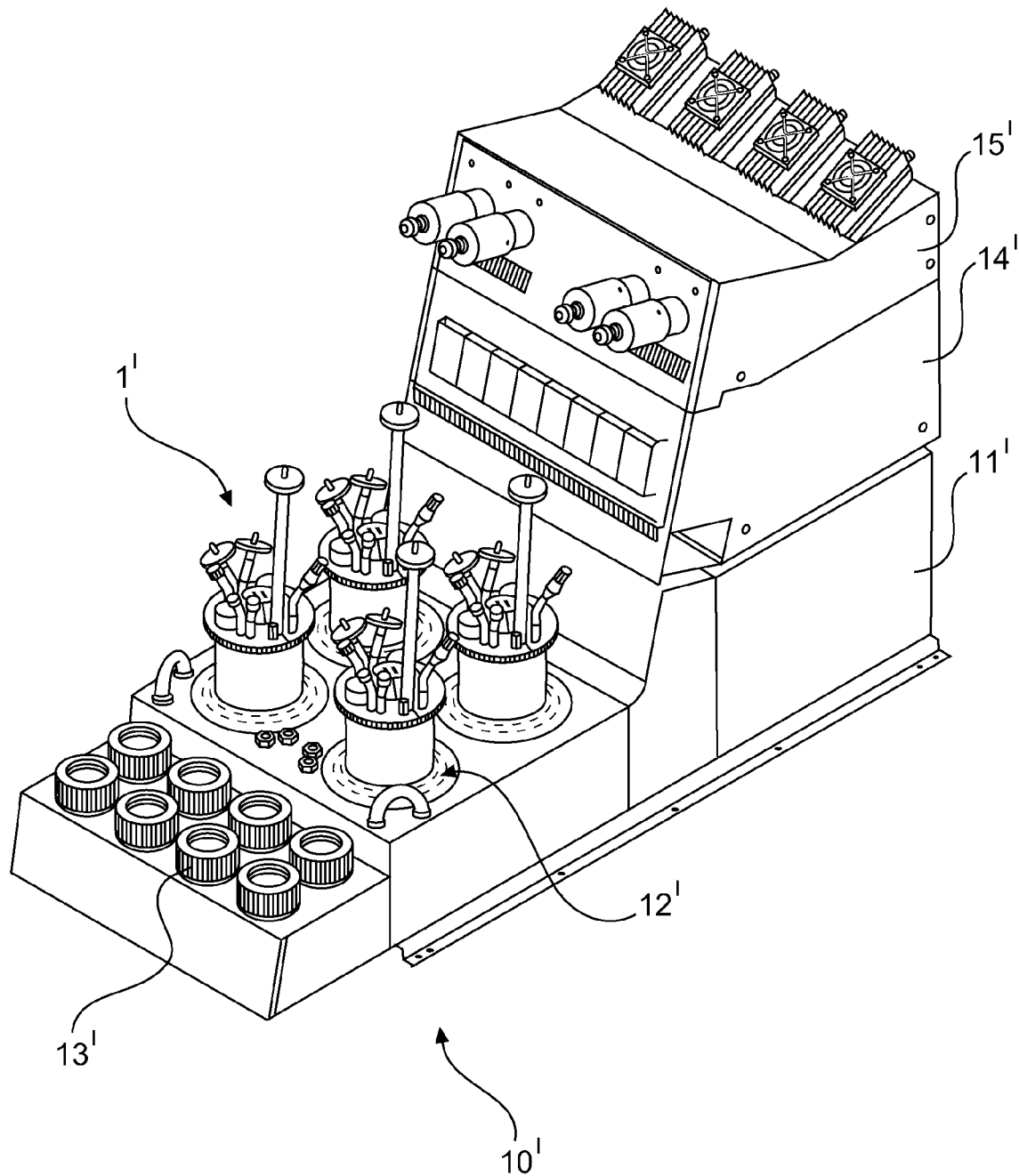
Figure 8:
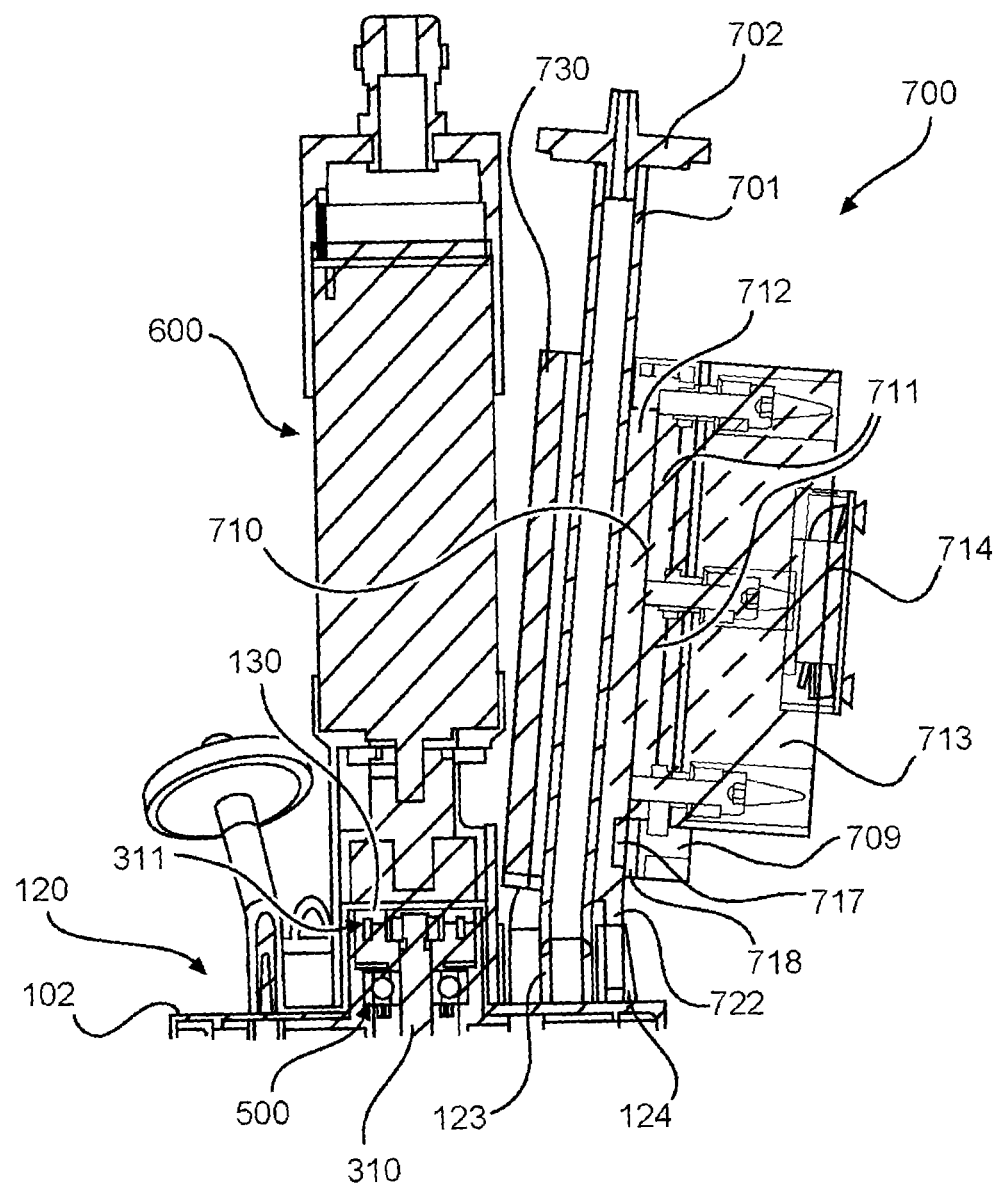
Figure 9A:
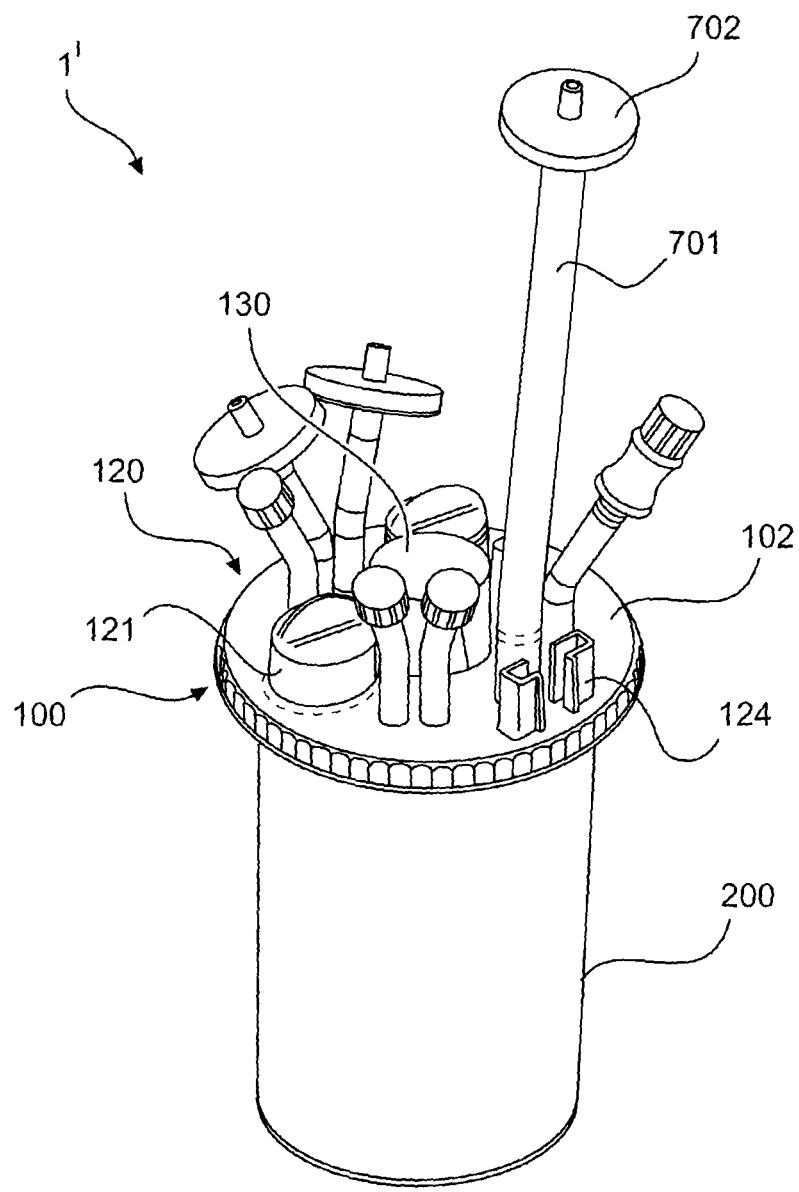
Figure 10:
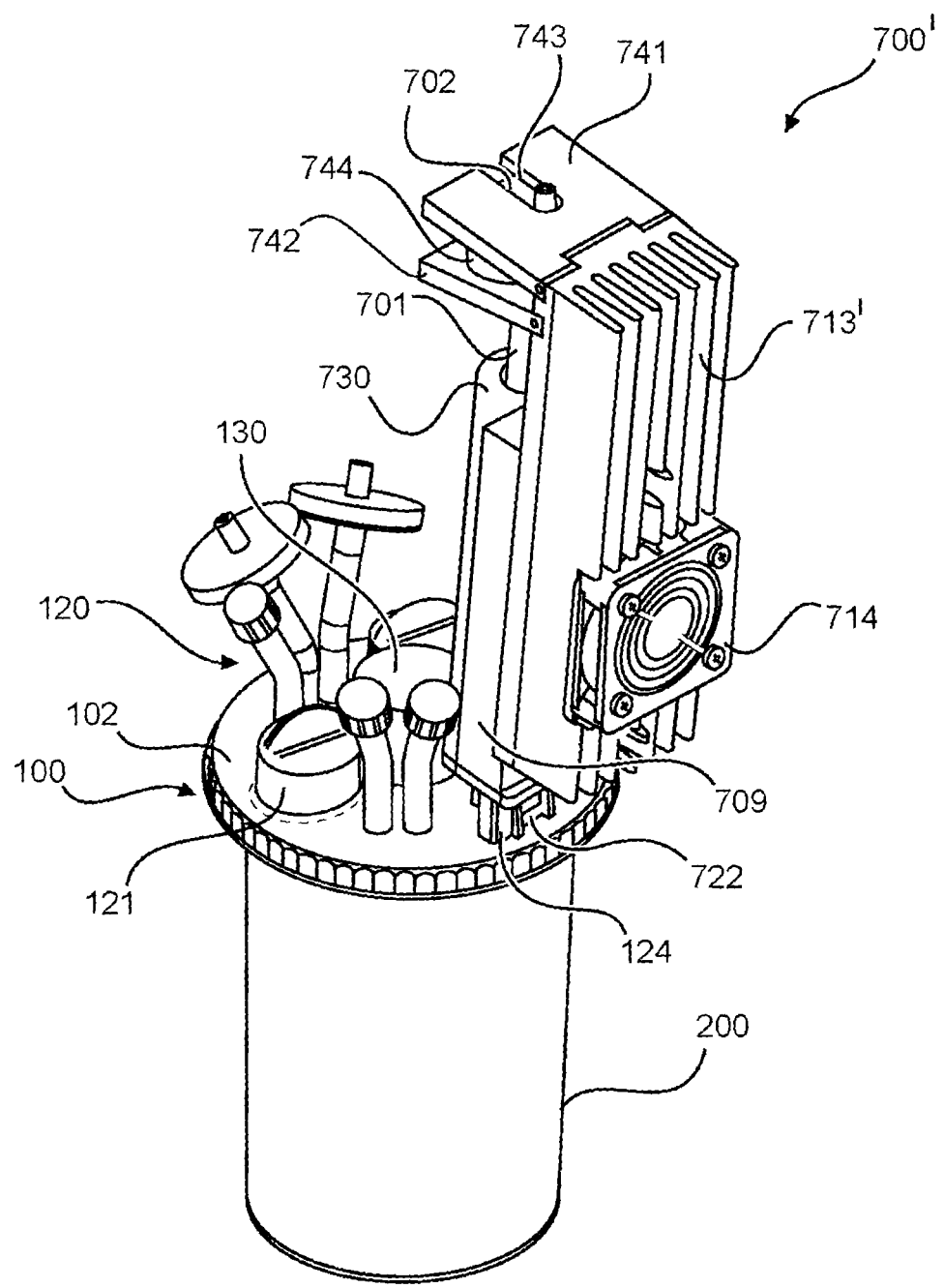
Figure 11:
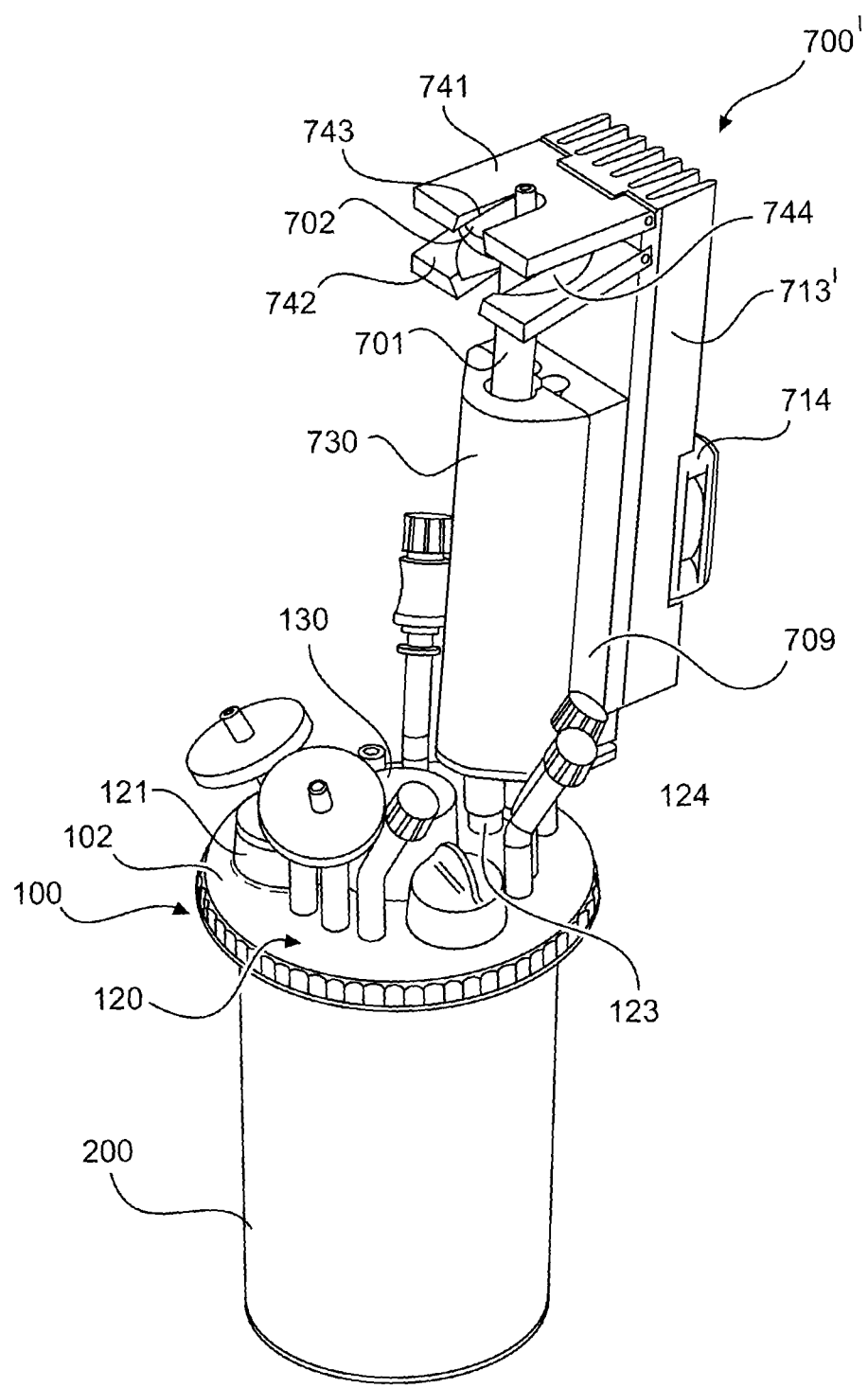

The invention shall now be described with reference to preferred embodiments and to the FIGS. 1-5, in which FIG. 1 shows a perspective view of a biotechnological apparatus comprising a bioreactor, FIG. 2 shows a perspective view of an arrangement comprising an exhaust gas conduit, and mounted thereon an exhaust gas temperature control device for the biotechnological apparatus in FIG. 1, FIG. 3 shows a perspective view of the arrangement in FIG. 2, in which the exhaust gas temperature control device is disconnected from the exhaust gas conduit, FIG. 4 shows a perspective view of the arrangement in FIG. 3 from a different perspective and FIG. 5 shows a sectional view of the arrangement in FIG. 2. Further preferred embodiments of the invention are described by way of example with reference to the attached FIGS. 6-11, in which:

FIG. 6A: shows a three-dimensional view of a biotechnological device comprising a single-use bioreactor, a connection device and a temperature control device;

FIG. 6B: shows a side view of the biotechnological device in FIG. 6A;

FIG. 6C: shows a plan view of the biotechnological device in FIG. 6A;

FIG. 6D: shows a cross-section of the biotechnological device in FIG. 6A along the sectional plane A-A in FIG. 6C;

FIG. 7: shows a parallel bioreactor system for use of the biotechnological device;

FIG. 8: shows an enlarged section from FIG. 6D;

FIG. 9A, B, C, D: show various steps in fitting a connection device and a temperature control device to an exhaust gas tube;

FIG. 10: shows a three-dimensional view of a connection device and a temperature control device with two heat transmission members; and FIG. 11: shows another three-dimensional view of the connection device and the temperature control device in FIG. 10.

FIG. 1 shows a perspective view of a biotechnological apparatus comprising a bioreactor 1, which in the embodiment shown is designed to be autoclavable. A reactor vessel 2 of bioreactor 1 is made of glass. Functional components are arranged in the usual manner in reactor vessel 2, in particular a stirrer 3. The following description applies accordingly to other bioreactor designs, such as single-use reactors or hybrid reactors, without these being shown explicitly in the Figures.

Inside cover 4, with which reactor vessel 2 is closed, a plurality of feedthroughs 5 are formed in order to supply the substances needed for the cultivation process and/or to remove substances from reactor vessel 2, for example gases produced during cultivation. On one feedthrough 6, there is arranged an exhaust gas conduit 7, in which an exhaust gas channel 8 is formed that is used to remove, in the form of a gas stream, gases that are produced in reactor vessel 2 during cultivation, for example water vapour.

Assigned to exhaust gas conduit 7 is an exhaust gas temperature control device 9, which is releasably mounted on exhaust gas conduit 7 and which is used to control the temperature of the exhaust gas stream flowing through exhaust gas channel 8, in particular in such a way that the exhaust gas stream condenses at least partially. The condensate thus produced can then be returned to reactor vessel 2, thus reducing, for example, the amount of water loss caused during cultivation by gassing.

FIGS. 2 to 5 show, in schematic views, further details of the arrangement comprising exhaust gas conduit 7 and the exhaust gas temperature control device 9 assigned thereto.

In the view shown in FIG. 2, the exhaust gas temperature control device 9 is mounted in operating position on exhaust gas conduit 7. FIG. 5 shows a sectional view of this arrangement.

In the views shown in FIGS. 3 and 4, exhaust gas temperature control device 9 is detached from exhaust gas conduit 7, as a result of which the thermal coupling between one temperature control surface 10 of a temperature control actuator 11 included in exhaust gas temperature control device 9 is disconnected from an associated support surface 12 of exhaust gas conduit 7. When the exhaust gas temperature control device 9 is mounted on exhaust gas conduit 7, both surfaces automatically come into overlapping contact, so that when the exhaust gas temperature control device 9 is fitted onto exhaust gas conduit 7, not only a mechanical attachment, but also a thermal coupling is automatically produced.

Temperature control actuator 11 may be designed with at least one Peltier element, for example. In the embodiment shown, exhaust gas temperature control device 9 also has a heat sink 13 and a fan assembly 14 disposed thereon.

The exhaust gas temperature control device 9 is fixed to the exhaust gas conduit 7 with the aid of a mechanical, self-locking connection which is produced, in the embodiment shown in FIGS. 3 and 4, by means of guide members 15, 16, which are formed on exhaust gas conduit 7 and on the exhaust gas temperature control device 9. Guide members 15, 16 engage each other positively when pushed onto the exhaust gas temperature control device 9, with the result that the exhaust gas temperature control device 9 can be pushed downwards bit by bit from above in a direction parallel to exhaust gas channel 8. In the embodiment shown, guide members 15, 16 are formed at the edges of the two surfaces which serve to produce the thermal coupling between exhaust gas conduit 7 and the exhaust gas temperature control device 9. A conical or wedge-shaped design of at least one guide member 15, 16 causes the opposite surfaces that heat is exchanged with to be pressed against each other.

In FIG. 4, a sensor member 17 is arranged on the exhaust gas temperature control device 9, in the lower region of support surface 12, which in conjunction with an associated sensor member 18 (cf. FIG. 5) on exhaust gas temperature control device 9 forms part of a sensor system which checks whether the exhaust gas temperature control device 9 is coupled or not coupled to exhaust gas conduit 7 and, in the event that it is decoupled, automatically deactivates temperature control actuator 11 in the exhaust gas temperature control device 9. Sensor member 17 is a light-reflecting mirror, for example, which reflects an optical signal transmitted by the associated sensor member 18 when the exhaust gas temperature control device 9 is connected. In another embodiment, sensor member 17 is provided in the form of a permanent magnet, which cooperates with a Hall sensor enclosed within associated sensor member 18.

FIG. 5 shows a cross-section of the arrangement in FIG. 2, from which it can be seen that in exhaust gas channel 8, in the axial direction of exhaust gas channel 8, projections 19 are formed which induce turbulence that optimises the transfer of heat. In the embodiment shown, projections 19 form a regular lateral arrangement in the axial direction of exhaust gas channel 8.

The features of the invention which are disclosed in the above description, in the claims and in the drawings may be material in their various embodiments, both separately and in any combination, for realising the invention.

FIGS. 6 to 11 show, by way of example, certain embodiments of the invention and how it is applied. Identical or similar elements are marked in the Figures with the same reference signs.

FIGS. 6A, 6B, 6C, 6D show a single-use bioreactor 1' comprising a head plate 100 and a container 200 which enclose a reaction chamber 400 in which a stirring member 320 of a mixer is arranged torsionally rigidly on a mixer shaft. Head plate 100 has an inner side 101 facing towards the reaction chamber, on which inner side a plurality of dip tubes 110 which project into reaction chamber 400 are arranged. A plurality of connectors 120 are arranged on an outer side 102 of head plate 100 facing towards reaction chamber 400. Head plate 100 is preferably of integral construction and preferably made of polyamide in an injection molding process, including the connectors 120 arranged on its outer side and the dip tubes 110 arranged on its inner side. Dip tubes 110 match a part of connectors 120, such that instruments, sensors, conduits or tubes can be inserted into and removed from the reaction chamber through corresponding connectors 120 and through dip tubes 110. Connectors 120 are used to provide the substances necessary for the reaction process and/or to remove substances, such as gases produced during operation, from reaction chamber 400. Connectors 120 can also be referred to as the overlay, and dip tubes 110 as submersibles.

Such a dimensionally stable single-use bioreactor, as is also described in the applicant's application EP12172304.3 entitled "Single-use bioreactor and head plate, and a process of manufacturing same", is suitable in particular for use in a parallel bioreactor system 10', such as the one shown in FIG. 7. The parallel bioreactor system 10' shown in FIG. 7 has a base block 11' with four receptacles 12' arranged therein, into each of which a single-use bioreactor 1' can be detachably inserted. A temperature control unit configured to heat or cool the bioreactors 1' arranged in receptacles 12', as required, is preferably arranged in base block 11'. An arrangement with containers 13' is formed adjacent to base block 11'. Base block 11' also includes a stacking surface on which two functional blocks 14', 15' are removably arranged in a stack, the latter being configured, for example, as a deposit and display station or a pump station, for example to supply or remove the fluid necessary for operating the single-use bioreactors. Such a parallel bioreactor system 10' has the advantage of having a high degree of scalability, since a plurality of these parallel bioreactor systems 10' each having four single-use bioreactors 1' can be arranged side by side.

As can be seen in FIG. 8, in particular, a temperature control device 700 comprising a central member 709 is detachably attached to a gas conduit, embodied here as an exhaust gas tube 701, and provided with a sterile filter 702 of a single-use bioreactor 1'. The following description shows the use of a temperature control device 700 and a connection device 720 for connection to a dimensionally stable single-use bioreactor 1' with a head plate 100. However, temperature control device 700 and connection device 720 may likewise be used with a single-use bioreactor with flexible walls, and is preferably connected in the latter case to a connection member. Use of the connection device and of the temperature control device to control the temperature of an exhaust gas stream in a flexible exhaust gas tube is likewise shown here. However, the connection device and the temperature control device may likewise be used to control the temperature of fluids in other fluid conduits and/or in other directions of flow, for example in a dimensionally stable feed pipe or exhaust pipe.

Figure 9B:
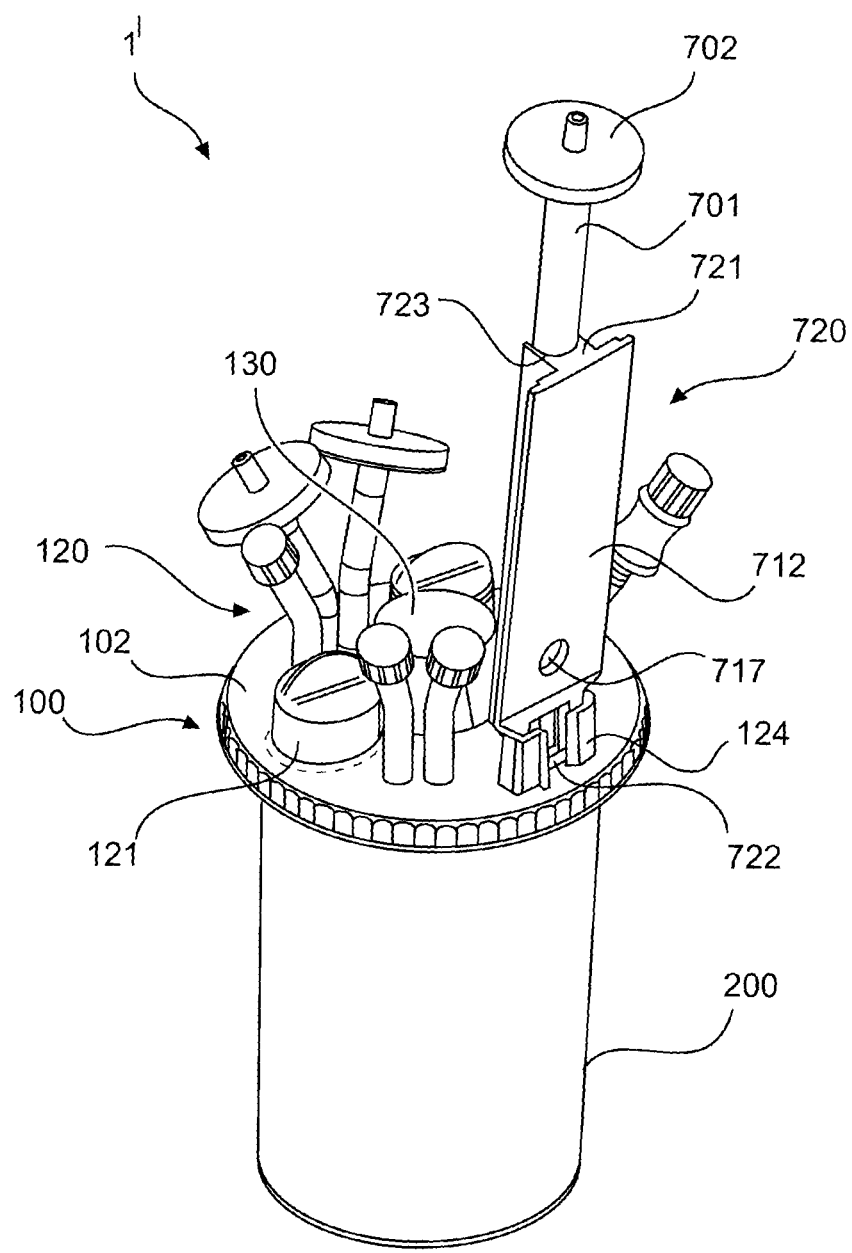
Figure 9C:
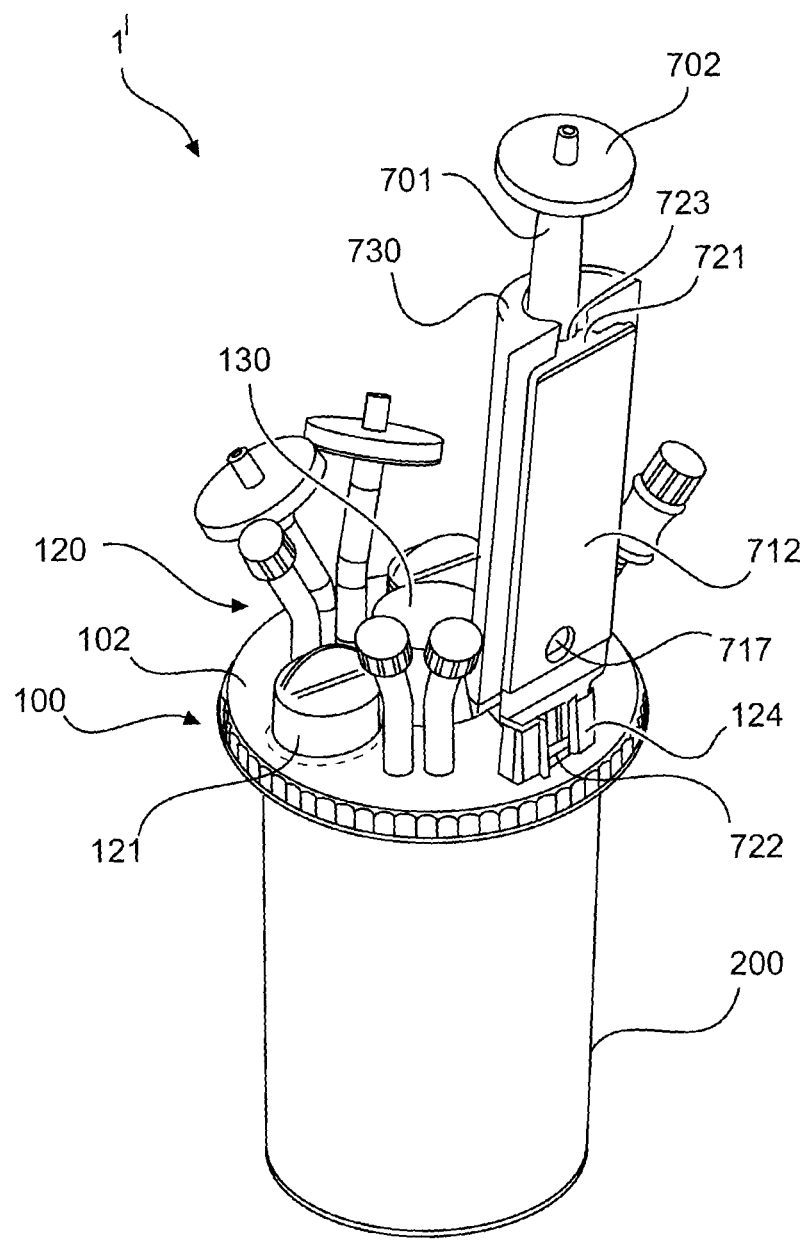
Figure 9D:
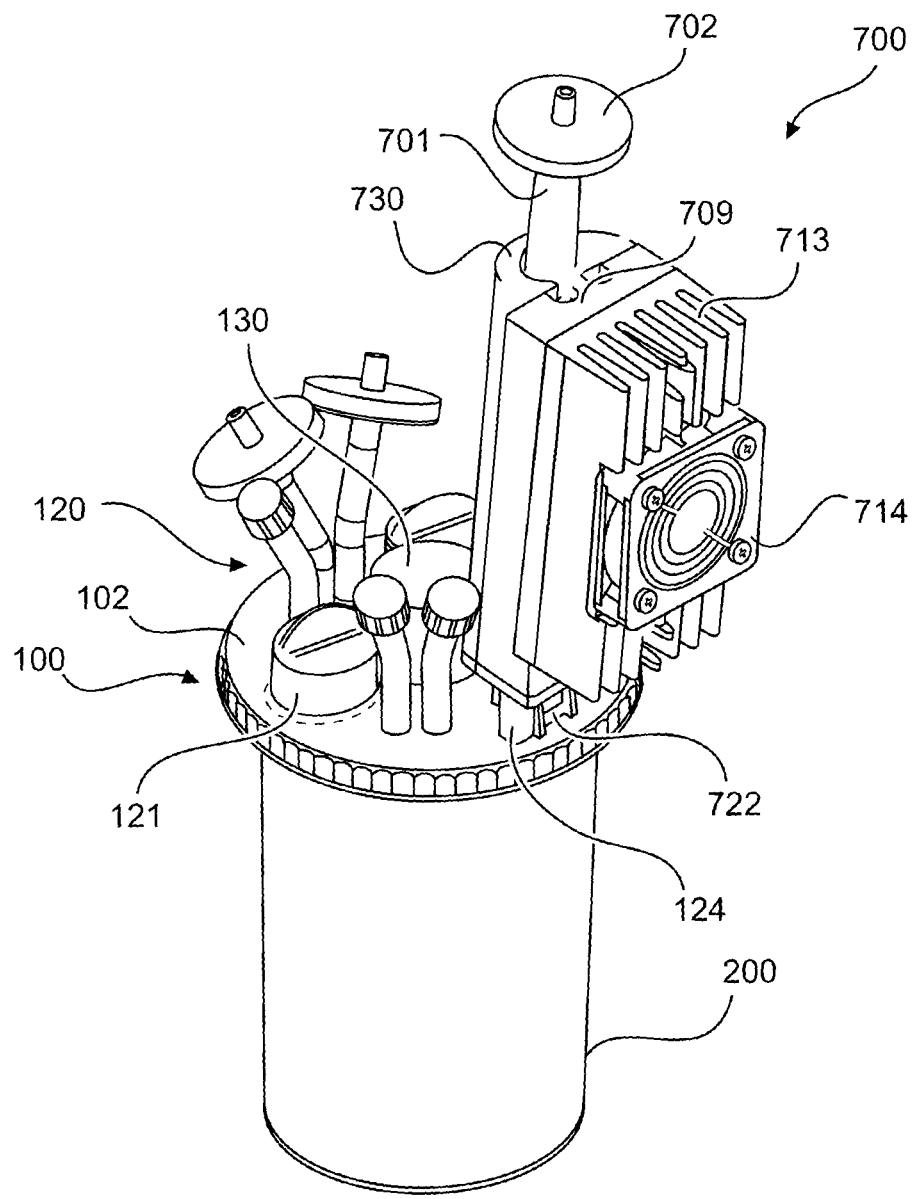

In the views shown in FIGS. 9A-9C, temperature control device 700 is detached from connection device 720, as a result of which the thermal coupling between a temperature control surface 710 of a temperature control actuator 711 included in temperature control device 700 is separate from coupling member 712 of connection device 720. When the temperature control device 700 is mounted on connection device 720, temperature control surface 710 and the coupling face of coupling member 712, embodied here as a flat surface, come into overlapping contact, so fitting temperature control device 700 to connection device 720 automatically produces not only a mechanical attachment, but also a thermal coupling.

Temperature control actuator 711 may be designed with at least one Peltier element, for example. In the embodiment shown, temperature control device 700 also has a heat sink 713 and a fan assembly 714 arranged thereon.

Temperature control device 700 is preferably attached to connection device 720 with the aid of a mechanical, self-locking connection. In FIG. 8 and FIGS. 9A-9C, in the lower region of coupling member 712, a sensor element 717 can be seen which in conjunction with an associated sensor element 718 (cf. FIG. 8) on temperature control device 700 forms part of a sensor system which checks whether the temperature control device 700 is connected or not connected to connection device 720 and, in the event that it is disconnected, automatically deactivates temperature control actuator 711 in temperature control device 700. Sensor element 717 is a light-reflecting mirror, for example, which reflects an optical signal transmitted by the associated sensor element 718 when the temperature control device 700 is connected. In another embodiment, sensor element 717 is provided with a permanent magnet which co-operated with a Hall sensor included in the associated sensor element 718.

The steps for manufacturing a attachment mechanism for connection device 720 and for temperature control device 700 are shown in FIGS. 9A-9D. A sterile, single-use bioreactor 1' is usually provided already with an exhaust gas tube 701 with a sterile filter 702 arranged thereon, said exhaust gas tube being likewise sterilized during the production process and attached to a connector 123 on head plate 100. Preserving the sterility of this system, including exhaust gas tube 701 and sterile filter 702, is of major importance for carrying out biological or biotechnological processes in the single-use bioreactor.

A connection device 720 with a receptacle 721 embodied as a longitudinal groove and comprising a coupling member 712 and a connecting section 722 can be detachably attached to the single-use bioreactor 1' without putting its sterility at risk. Connecting section 722 is inserted into a connection slot 124 provided for that purpose on head plate 100. The flexible exhaust gas tube 701 is also pressed in portions thereof into receptacle 721 in a direction running substantially orthogonally to a longitudinal axis of connection device 720, in such a way that exhaust gas tube 701 is preferably clamped into receptacle 721. A contact surface 723 of receptacle 721 preferably contacts a respective area of an outer surface of exhaust gas tube 701, in order to provide optimal heat transfer between exhaust gas tube 701 and connection device 720. The longitudinal extension of connection device 720 is shorter than an extension of exhaust gas tube 701 between its connection to single-use bioreactor 1' and a sterile filter 702 arranged on exhaust gas tube 701. However, the longitudinal extension of connection device 720 amounts to most of the length of exhaust gas tube 701 between its connections to single-use bioreactor 1' and to sterile filter 702, in order to have a greater contact surface and hence to achieve better heat transfer. Connection device 720 is preferable made of aluminum.

Connection device 720 may also be embodied in two parts, for example, in order to cradle exhaust gas tube 701 around its entire circumference if possible, preferably by clamping and/or by form-locking effect. The two parts are then preferably designed to be joined together in a direction running substantially orthogonally to a longitudinal axis of connection device 720 and to receive the portion of exhaust gas tube 701 in receptacle 721.

A thermal insulation member 730 is arranged in a next step in order to increase the thermal efficiency and to prevent condensation from forming on the outside. Thermal insulation member 730 may likewise be provided with a longitudinal groove and may likewise be connected by clamping and/or by form-locking effect to exhaust gas tube 701 and/or to connection device 720.

Thermal insulation member 730 is preferably made of materials that conduct poorly, such as foamed polymers. A temperature control device 700 can now be arranged on coupling member 712 of connection device 720 with good thermal coupling, and preferably detachably. The configuration of temperature control device 700, comprising temperature control actuator 711 preferably embodied as a Peltier element, a heat transmission body or heat sink 713 and a fan assembly 714 arranged thereon, may preferably be the same as the temperature control device described in application DE 10 2011 054 364.3.

FIGS. 10 and 11 show one variant of temperature control device 700' in which heat transfer body 713' is extended in length, and on which two heat transmission members 741, 742 are mounted rotatably about a horizontal axis, said heat transmission members being of plate-shaped design with slots, and able to cradle sterile filter 702 at least in sections thereof. Further, the first heat transmission member 741 comprises on its respective side facing the sterile filter 702 an indentation 743 for receiving at least a part of the sterile filter 702, wherein the indentation 743 preferably is formed as a counterpart to the part of the sterile filter 702 to be received therein. Likewise, the second heat transmission member 742 comprises on its respective side facing the sterile filter 702 an indentation 744 for receiving at least a part of the sterile filter 702. Also, the indentation 744 of the second heat transmission member 742 preferably is formed as a counterpart to the part of the sterile filter 702 to be received therein.

This has the advantage that any waste heat arising when exhaust gas is cooled to recover condensate is not simply dissipated, but is used to heat the sterile filter. The thermal coupling of heat transmission members 741, 742 and temperature control actuator 711, preferably the warm side of the temperature control actuator, is preferably effected via heat sink 713'. The arrangement of two heat transmission members 741, 742 preferably on two different sides of sterile filter 702 results in improved, more uniform heating of sterile filter 702.

The features of the invention which are disclosed in the above description, in the claims and in the drawings may be material in their various embodiments, both separately and in any combination, for realizing the invention.

The invention claimed is:

1. A biotechnological device comprising:
a single-use bioreactor provided with a sterile single-use fluid conduit, a temperature control device and a reusable connection device having a longitudinal axis, the connection device being configured to operably connect the temperature control device to the sterile single-use fluid conduit of the single-use bioreactor,
the connection device comprising:
a thermal insulation member comprising a recess configured to receive a portion of the sterile single-use fluid conduit;
a receptacle in which a portion of the sterile single-use fluid conduit is arranged, and a coupling member having a coupling face arranged and configured to operably connect the connection device to the temperature control device, wherein the sterile single-use fluid conduit includes a gas conduit, and the gas conduit includes a flexible tube or a dimensionally stable pipe, wherein the flexible tube or the dimensionally stable pipe is arranged between the thermal insulation member and the temperature control device; and
wherein the thermal insulation member is detachably connected to the connection device and surrounding a portion of the receptacle of the connection device,
wherein the temperature control device is detachably connected to the connection device,
wherein the receptacle has a contact surface which is arranged and configured in such a way that the contact surface abuts the sterile single-use fluid conduit, the receptacle supporting at least a portion of length of the single-use fluid conduit proximal to the single-use bioreactor in an upright position wherein a fluid channel defined by the single-use fluid conduit is positioned in a direction from the single-use bioreactor towards the temperature control device so that gas exhausts upward from the single-use bioreactor into the fluid channel and condensate flows downward from the fluid channel into the single-use bioreactor,
wherein the receptacle is arranged and configured in such a way that a portion of the sterile single-use fluid conduit is detachably introduced into the receptacle in a direction running orthogonally to the longitudinal axis, and
wherein the receptacle has a first and a second part, the first and second parts being designed to be joined together in a direction running orthogonally to a longitudinal axis of the connection device and to receive a portion of the sterile single-use fluid conduit in the receptacle.

2. The biotechnological device according to claim 1, wherein the connection device comprises a material having a thermal conductivity of more than 10 W/(m*K).

3. The biotechnological device according to claim 1, wherein the connection device has a longitudinal extension which is shorter than an extension of the sterile single-use fluid conduit between a connection of the sterile single-use fluid conduit to the single-use bioreactor and to a sterile filter arranged on the sterile single-use fluid conduit.

4. The biotechnological device according to claim 1, wherein the connection device further comprising a bottom section adapted and arranged to detachably attach to receiving slots of the single-use bioreactor.

5. The biotechnological device according to claim 1, the temperature control device having activated and deactivated states, the temperature control device being configured to enter the deactivated state upon disconnection from the receptacle.

6. The biotechnological device according to claim 5, further comprising:
a heat transmission member thermocouplingly connected to the temperature control device, the heat transmission member arranged to transfer heat from the temperature control device to a sterile filter operably connected to the single-use fluid conduit.

7. The biotechnological device according to claim 6 wherein the temperature control device comprises a heat sink.

8. The biotechnological device according to claim 6 wherein the heat transmission member comprises first and second heat transmission members and define a gap between the first and second heat transmission members, the gap sized and arranged to receive the sterile filter.

9. The biotechnological device according to claim 1, further comprising a cooler operably connected to the receptacle.

10. The biotechnological device according to claim 9, wherein the cooler is a temperature control actuator having activated and deactivated states, the temperature control device actuator being configured to enter the deactivated state upon disconnection from the receptacle.

11. The biotechnological device according to claim 9, wherein the cooler is selected from a heat sink, a heat transmission body, a fan, a Peltier element, and combinations thereof.

12. The biotechnological device according to claim 11, wherein the cooler is detachably connected to the receptacle.

* * * * *

UNITED STATES PATENT AND TRADEMARK OFFICE
CERTIFICATE OF CORRECTION

PATENT NO. : 10,717,960 B2
APPLICATION NO. : 14/351086
DATED : July 21, 2020
INVENTOR(S) : Matthias Arnold et al.

Page 1 of 1

It is certified that error appears in the above-identified patent and that said Letters Patent is hereby corrected as shown below:

In the Specification

Column 1, Line 11, after "Ser. No." delete "12/172,291.2" and insert --12127291.2--

In the Claims

Column 23, Line 4, Claim 10 after "device" delete "actuator"

Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*